(12) United States Patent
Maecker et al.

(10) Patent No.: US 10,215,758 B2
(45) Date of Patent: Feb. 26, 2019

(54) PLATINUM-LABELED PROBES FOR MASS CYTOMETRY

(71) Applicant: The Board of Trustees of the Leland Stanford Junior University, Stanford, CA (US)

(72) Inventors: Holden Terry Maecker, Palo Alto, CA (US); Michael Duane Leipold, San Francisco, CA (US); Henrik Mei, Berlin (DE)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 122 days.

(21) Appl. No.: 15/231,489

(22) Filed: Aug. 8, 2016

(65) Prior Publication Data

US 2017/0059574 A1    Mar. 2, 2017

Related U.S. Application Data

(60) Provisional application No. 62/209,601, filed on Aug. 25, 2015.

(51) Int. Cl.
| | |
|---|---|
| *G01N 33/58* | (2006.01) |
| *G01N 33/60* | (2006.01) |
| *G01N 30/72* | (2006.01) |
| *G01N 33/534* | (2006.01) |
| *G01N 33/53* | (2006.01) |
| *G01N 33/68* | (2006.01) |

(52) U.S. Cl.
CPC ....... *G01N 33/585* (2013.01); *G01N 33/6848* (2013.01); *G01N 33/53* (2013.01)

(58) Field of Classification Search
CPC ..... G01N 33/58–33/588; G01N 33/53–33/553
See application file for complete search history.

(56) References Cited

U.S. PATENT DOCUMENTS

| | | | | |
|---|---|---|---|---|
| 5,714,327 | A * | 2/1998 | Houthoff | ............. C07F 15/0093 435/6.1 |
| 2013/0315820 | A1 | 11/2013 | Fournier et al. | |
| 2014/0329272 | A1 | 11/2014 | Bodenmiller et al. | |
| 2015/0080233 | A1 | 3/2015 | Bendall et al. | |

FOREIGN PATENT DOCUMENTS

| | | | | |
|---|---|---|---|---|
| EP | 1505394 A1 * | 2/2005 | ........... | G01N 33/533 |
| WO | WO-02069898 A2 * | 9/2002 | ........... | C07F 15/0093 |

OTHER PUBLICATIONS

Beavis et al. Detection of cell-surface antigens using antibody-conjugated fluorospheres (ACF): application for six-color immunofluorescence. Biotechniques 1996, vol. 21, pp. 498-503. (Year: 1996).*

Beck et al. "In vitro activity of immunoconjugates between cisplatin and an anti-CA125 monoclonal antibody on ovarian cancer cell lines", Cell Biophysics, vol. 24-25, No. 1-3, pp. 163-173 (1994).

Fienberg et al. "A platinum-based covalent viability reagent for single cell mass cytometry", Cytometry, Part A, vol. 81, pp. 467-475 (2012).

Mei et al. "Platinum-conjugated Antibodies for Application in Mass Cytometry", Cytometry, Part A, vol. 89, No. 3, pp. 292-300 (2015).

* cited by examiner

*Primary Examiner* — Shafiqul Haq
(74) *Attorney, Agent, or Firm* — Michael J. Blessent; Bret E. Field

(57) ABSTRACT

The present disclosure provides analyte-specific binding reagents conjugated with a platinum-containing moiety, e.g., cisplatin, and methods, compositions, and kits for their production and use in assays for analyte detection.

16 Claims, 7 Drawing Sheets

PLATINUM-LABELED PROBES FOR MASS CYTOMETRY

CROSS-REFERENCING

This application claims the benefit of U.S. provisional application Ser. No. 62/209,601, filed on Aug. 25, 2015, which application is incorporated by reference herein.

GOVERNMENT RIGHTS

This invention was made with Government support under contracts RR027582 and TR001085 awarded by the National Institutes of Health. The Government has certain rights in the invention.

BACKGROUND

Mass cytometry permits high-dimensional analysis of single cell suspensions, much like conventional fluorescence-based flow cytometry (see, e.g., Bendall et al., "Single-cell mass cytometry of differential immune and drug responses across a human hematopoietic continuum.", Science 2011; 332:687-96; and Tanner et al., "Flow cytometer with mass spectrometer detection for massively multiplexed single-cell biomarker assay.", Pure and Applied Chemistry 2008; 80:2627-2641). For a mass cytometry experiment, a cell sample is incubated with specific metal-containing probes, usually metal-labeled antibodies (Ab), which bind to their cellular targets and report their presence by quantifying the metal associated with the cell during sample acquisition on the mass cytometer. However, usable mass ranges in version 1 and 2 CyTOF platforms (Fluidigm; South San Francisco, Calif.) comprise 92 and 121 mass channels, respectively, which are far from being fully occupied with reagents. Some channels are not suited for reporting of specific probes due to the overlap with the detection of traces of xenon in argon (AM 128-132, 134, 136) or barium (AM 134-138), being an unwanted yet frequent metal contaminant. The use of some elements such as Pb, Hg and Tl appears limited due to their toxicity for cells and eventually users.

There is a general need for better exploitation of the analytical capacity of mass cytometers, and additional channels available for reporting specific probes would be undoubtedly useful.

SUMMARY

Provided in this disclosure are analyte-specific binding reagents conjugated with a platinum-containing moiety, e.g., cisplatin, in which the platinum-containing moiety, when conjugated to the analyte-specific binding reagent, does not have covalent binding activity. Methods, compositions, and kits for the production and use of such platinum-conjugated analyte-specific binding reagents in assays for analyte detection are also disclosed.

A method of detecting the presence of an analyte on a particle, the method comprising: contacting a particle with an analyte-specific binding reagent conjugated to a platinum-containing moiety under conditions sufficient for analyte-specific binding of the analyte-specific binding reagent to its cognate analyte, wherein the platinum-containing moiety, when conjugated to the analyte-specific binding reagent, does not have covalent binding activity; and determining if platinum is associated with the particle, wherein when platinum is associated with the cell the analyte is present on the particle.

In certain embodiments, the method further comprises isolating the particle based on the presence of the presence, level, or absence of platinum associated with the particle.

In certain embodiments, the platinum-containing moiety is conjugated directly to the analyte-specific binding reagent.

In certain embodiments, the analyte-specific binding reagent is an antibody. In certain embodiments, the antibody is a phospho-specific antibody. In certain embodiments, the analyte-specific binding reagent is an MHC multimer/tetramer. In certain embodiments, the analyte-specific binding reagent is a nucleic acid.

In certain embodiments, the analyte-specific binding reagent is a member of a binding pair employed in secondary detection methods, including but not limited to the following: biotin and avidin or streptavidin; lectin; anti-digoxin or anti-digoxigenin antibody; and anti-fluorochrome antibody.

In certain embodiments, the particle is a cell. In certain embodiments, the analyte is on the cell surface. In certain embodiments, the analyte is intracellular, wherein the method further comprises permeabilizing the cell. In certain embodiments, the analyte is a soluble molecule.

In certain embodiments, the analyte is a protein. In certain embodiments, the analyte is a phospho-specific isoform of the protein. In certain embodiments, the analyte is a nucleic acid. In certain embodiments, the analyte is a carbohydrate. In certain embodiments, the analyte is a small molecule. In certain embodiments, the analyte is an organic compound.

In certain embodiments, the analyte is a member of a binding pair employed in secondary detection methods, including but not limited to the following: biotin and avidin or streptavidin; carbohydrate; digoxin or digoxigenin; and fluorochrome. In such embodiments, the analyte-specific binding reagent employed to detect the analyte is the cognate member of the binding pair.

In certain embodiments, the cell is present in a heterogeneous population of particles.

In certain embodiments, the platinum in the platinum-containing moiety is a mixture of isotopes. In certain embodiments, the platinum in the platinum-containing moiety is synthetically enriched for a specific isotope. In certain embodiments, the in the platinum-containing moiety is selected from the group consisting of: cisplatin, carboplatin, oxaliplatin, nedaplatin, lobaplatin, heptaplatin, satraplatin, picoplatin, prolindac, lipoplatin, JM-11, NSC 170898, ormaplatin, sebriplatin, enloplatin, zeniplatin, spiroplatin, cycloplatam, miboplatin, iproplatin, TRK-710, SPI-77, aroplatin, and BBR3464. In certain embodiments, the platinum-containing moiety is cisplatin.

In certain embodiments, multiple analyte-specific binding reagents are contacted with the particle, wherein each analyte-specific binding reagent is distinguishably labeled. In certain embodiments, each analyte-specific binding reagent is distinguishably labeled with a different platinum isotope.

In certain embodiments, the determining step is performed by elemental mass spectrometry-based detection. In certain embodiments, the detection is performed by inductively coupled plasma mass spectrometry, secondary ion mass spectrometry, thermal ionization mass spectrometry, or atomic absorption mass spectrometry. In certain embodiments, the detection is performed by mass cytometry.

In certain embodiments, the method further includes analyzing the particle for additional analytes by elemental or fluorescent detection.

Aspects of the present disclosure include a method of detecting a characteristic of particles in multiple particle-containing samples, the method comprising: a) contacting multiple particle-containing samples with corresponding analyte-specific binding reagent conjugated directly to a platinum-containing moiety under conditions sufficient for analyte-specific binding of the analyte-specific binding reagent to its cognate analyte, wherein the platinum isotope of each corresponding analyte-specific binding reagent for each of the multiple particle-containing samples is distinguishable; b) combining the multiple particle-containing samples to produce a combined sample; c) analyzing the particles in the combined sample to detect: i) the platinum isotope associated with each particle; and ii) at least one second detectable characteristic; to obtain a result, wherein detection of the platinum isotope does not interfere with detection of the at least one second detectable characteristic, and d) deconvoluting the result based on the detected platinum isotope, thereby detecting the at least one second detectable characteristic of the particles in each of the multiple particle-containing samples.

Aspects of the present disclosure include an analyte-specific binding reagent conjugated to a platinum-containing moiety, wherein the platinum-containing moiety does not have covalent binding activity. In certain embodiments, the platinum-containing moiety is selected from the group consisting of: cisplatin, carboplatin, oxaliplatin, nedaplatin, lobaplatin, heptaplatin, satraplatin, picoplatin, prolindac, lipoplatin, JM-11, NSC 170898, ormaplatin, sebriplatin, enloplatin, zeniplatin, spiroplatin, cycloplatam, miboplatin, iproplatin, TRK-710, SPI-77, aroplatin, and BBR3464. In certain embodiments, the platinum-containing moiety is cisplatin. In additional embodiments, the platinum containing moiety is a platinum salt, elemental platinum, or platinum nanocrystal.

Aspects of the present disclosure include a kit for use in any of the methods disclosed herein, where the kit comprises an analyte-specific binding reagent conjugated to a platinum-containing moiety, wherein the platinum-containing moiety does not have covalent binding activity.

BRIEF DESCRIPTION OF THE FIGURES

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures.

DEFINITIONS

Figure 1:
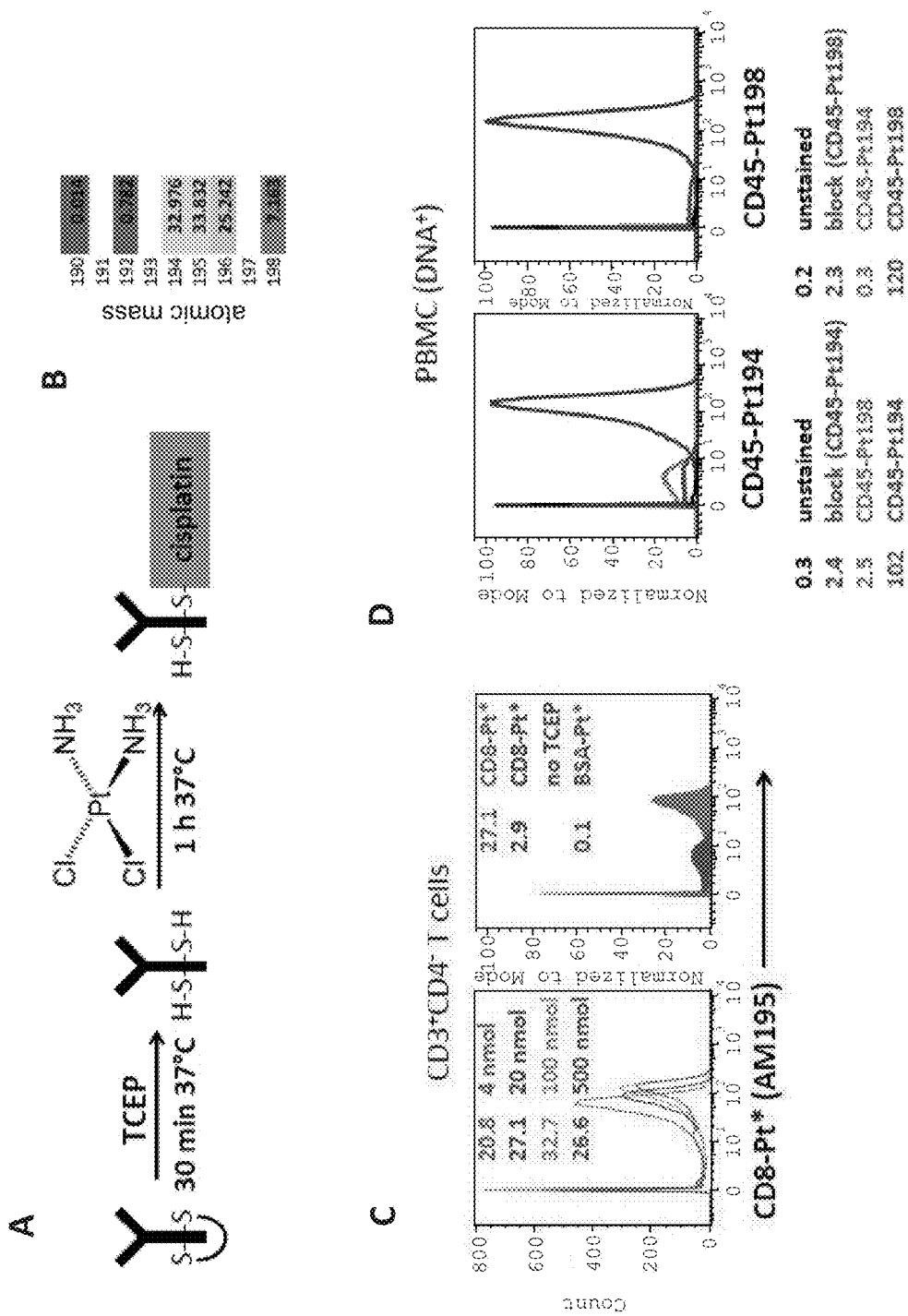
FIG. 1, Panels A-D. Production and validation of cisplatin-antibody conjugates for mass cytometry. (Panel A) Workflow for the platinum labeling of Ab using cisplatin. Upon treatment with TCEP, disulfide bonds are converted into free thiols, which serve as targets for cisplatin binding. (Panel B) Platinum occurs in six stable isotopes, the relative contribution of which to natural abundance platinum is depicted. Numbers indicated percentages (Panel C) Anti-CD8 Ab was labeled with natural abundance cisplatin (Pt*) using indicated amounts of cisplatin in the labeling reaction. PBMC were stained with the different CD8 conjugates at 5 µg/mL along with an Ab cocktail permitting gating of CD3+CD20−CD4− T cells. Numbers reflect geometric mean signal intensities (geoMSI). On the right, the staining with a regular CD8-Pt* Ab conjugate (20 nmol) is compared to stainings with BSA-Pt* and a CD8-Pt* for the production of which the TCEP reduction step of the Ab was omitted. As expected, BSA-Pt* shows no meaningful staining. The staining without reduction in the conjugation procedure is impaired. (Panel D) CD45 Ab was labeled with either cisplatin (AM194) or cisplatin (AM198). PBMC were stained with the conjugates. Blocking experiments with unlabeled Ab confirm the target specificity of the conjugates, and AM194- or AM198-only stained samples reveal mutual introduction of only minimal background. Numbers reflect geoMSI.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs.

As used herein, the term "labeling" refers to attaching a detectable moiety to an analyte such that the presence and/or abundance of the analyte can be determined by evaluating the presence and/or abundance of the label. The term "labeling" includes labeling using a histological stain (in which case the mass tag may be part of or conjugated to the stain) as well as labeling using a capture agent, e.g., an antibody or an oligonucleotide probe, that has been conjugated to a mass tag. A sample can also be labeled by feeding the sample with a mass-tagged compound (e.g., IdU or BrdU) that is metabolized and incorporated into the sample prior to fixation. An analyte may also be labeled in vivo by providing a detectable analyte-specific binding reagent to a live organism, e.g., an animal or plant. For example, labeled analyte-specific binding reagents can be administered in vivo to detect the distribution of therapeutic antibodies into body/tumor compartments.

As used herein, the term "multiplexing" refers to using more than one label for the simultaneous or sequential detection and measurement of more than one analyte.

As used herein, the terms "binding reagent", "analyte-specific binding reagent", "specific binding reagent", "specific binding agent", "analyte binding agent", and the like, refer to a reagent that can specifically bind to one or more sites in a specific molecular target (e.g., a specific protein, phospholipid, DNA molecule, or RNA molecule) in or on a cell. Analyte-specific binding reagents can be labeled, e.g., conjugated covalently to a detectable moiety. Analyte-specific binding reagents include antibodies, nucleic acids, and aptamers, for example. A used herein, an "aptamer" is a synthetic oligonucleotide or peptide molecule that specifically binds to a specific target molecule. As used herein, the terms "antibody" and "immunoglobulin" are used interchangeably herein and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, minibodies, single-chain antibodies, engineered or glyco-engineered antibodies or antigen binding fragments thereof, and fusion proteins comprising an antigen-binding portion of an antibody and a non-antibody protein. Also encompassed by the term are Fab', Fv, F(ab')$_2$, and or other antibody fragments that retain specific binding to antigen, and monoclonal antibodies. Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e. g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986),).

The term "specific binding" or "analyte-specific binding" refers to the ability of a binding reagent to preferentially bind to a particular analyte that is present in a homogeneous mixture of different analytes. In certain embodiments, a specific binding interaction will discriminate between desirable (target) and undesirable (non-target) analytes in a sample, in some embodiments more than about 10 to 100-fold or more (e.g., more than about 1000- or 10,000-fold).

In certain embodiments, the affinity between a binding reagent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

The term "specific binding member" as used herein refers to a member of a specific binding pair, i.e. two molecules, usually two different molecules, where one of the molecules through chemical or physical means specifically binds to the other molecule. For the purposes of the present invention, one of the molecules is an analyte as defined above, and generally the specific binding member is labeled for detection of fluorescence or elemental analysis, as known in the art.

The complementary (or cognate) members of a specific binding pair are sometimes referred to as a ligand and receptor; or receptor and counter-receptor. Specific binding indicates that the agent can distinguish a target antigen, or epitope within it, from other non-target antigens. It is specific in the sense that it can be used to detect a target antigen above background noise ("non-specific binding"). For example, a specific binding partner can detect a specific sequence or a topological conformation. A specific sequence can be a defined order of amino acids or a defined chemical moiety [e.g., a phospho-specific antibody (e.g., an antibody that recognizes a phosphotyrosine or a phosphoserine) or an antibody that recognizes a particular carbohydrate configuration, etc.] which occurs in the target antigen. The term "antigen" is issued broadly, to indicate any agent which elicits an immune response in the body. An antigen can have one or more epitopes.

Binding pairs of interest include antigen and antibody specific binding pairs, complementary nucleic acids, peptide-MHC-antigen complexes and T cell receptor pairs, biotin and avidin or streptavidin; carbohydrates and lectins; digoxin or digoxigenin and anti-digoxin or anti-digoxigenin antibodies; complementary nucleotide sequences; peptide ligands and receptor; effector and receptor molecules; hormones and hormone binding protein; enzyme cofactors and enzymes; enzyme inhibitors and enzymes; and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc., so long as an epitope is present.

Immunological specific binding pairs include antigens and antigen specific antibodies; and T cell antigen receptors, and their cognate MHC-peptide conjugates. Suitable antigens may be haptens, proteins, peptides, carbohydrates, etc. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic/genetically engineered organisms (e.g., animals, plants, bacteria, yeast, or other cell-based protein production systems), immunized animals, immortalized human or animal B-cells, cells transfected with DNA vectors encoding the antibody or T cell receptor, etc. The details of the preparation of antibodies and their suitability for use as specific binding members are well-known to those skilled in the art.

A nucleic acid based binding partner such as an oligonucleotide can be used to recognize and bind DNA or RNA based analytes. The term "polynucleotide" as used herein may refer to peptide nucleic acids, locked nucleic acids, modified nucleic acids, and the like as known in the art. The polynucleotide can be DNA, RNA, LNA or PNA, although it is not so limited. It can also be a combination of one or more of these elements and/or can comprise other nucleic acid mimics.

Binding partners can be primary or secondary. Primary binding partners are those bound to the analyte of interest. Secondary binding partners are those that bind to the primary binding partner.

As used herein, the term "mass tagged" refers to a molecule, e.g., an analyte-specific binding reagent, that is tagged with either a single kind of stable isotope that is identifiable by its unique mass or mass profile or a combination of the same, where the combination of stable isotopes provides an identifier. Mass tags can be covalently or non-covalently conjugated to a molecule (e.g., a binding reagent). Combinations of stable isotopes permit channel compression and/or barcoding. Examples of elements that are identifiable by their mass include noble metals and lanthanide, although other elements may be employed. An element may exist as one or more isotopes, and this term also includes isotopes of positively and negatively metals. The terms "mass tagged" and "elementally tagged" may be used interchangeably herein.

As used herein, the term "mass tag" means any isotope of any element, including transition metals, post transition metals, halides, noble metal or lanthanide, that is identifiable by its mass, distinguishable from other mass tags, and used to tag a biologically active material or analyte. A mass tag has an atomic mass that is distinguishable from the atomic masses present in the analytical sample and in the particle of interest. The term "monoisotopic" means that a tag contains a single type of metal isotope (although any one tag may contain multiple metal atoms of the same type).

As used herein, the term "lanthanide" means any element having atomic numbers 58 to 71. Lanthanides are also called "rare earth metals".

As used herein, the term "noble metal" means any of several metallic elements, the electrochemical potential of which is much more positive than the potential of the standard hydrogen electrode, therefore, an element that resists oxidation. Examples include palladium, silver, iridium, platinum and gold.

As used herein, the term "elemental analysis" refers to a method by which the presence and/or abundance of elements of a sample are evaluated.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

As used herein, the term "particle" refers to a three dimensional object in the range of 100 nm to 1 mm, e.g., 1 μm to 100 μm, in size. Single cells, which may be living or fixed, polymer beads, magnetic beads, etc., are examples of particles.

A "cell" or "sample comprising cells" or "cell sample" is a sample containing at least one intact cell of biological origin. The cell(s) may be viable or may be non-viable, e.g., permeabilized and/or fixed. In some embodiments, the sample may be a liquid sample, e.g., a cell suspension, while in other embodiments the sample may be substantially planar, e.g., cells on a slide, well plate, or other planar surface. Examples of such samples include tissue sections, samples that are made by depositing disassociated cells onto a planar surface, and samples that are made by growing a sheet of cells on a planar surface. In certain embodiments, a cell employed in the disclosed methods is present in vivo, i.e., in a living organism.

The term "flow cytometry" as used herein refers to a method and a process whereby cells within a sample can be detected and identified when transversing past a detector within an apparatus containing a detecting source and a flowing apparatus.

The term "fluorescently activated cell sorting assay" (FACS) as used herein refers to any assay suitable for use in cell sorting techniques (e.g., flow cytometry) that employs detection of fluorescent signals.

Other definitions of terms may appear throughout the specification.

DETAILED DESCRIPTION

As summarized above, the present disclosure provides analyte-specific binding reagents conjugated with a platinum-containing moiety, e.g., cisplatin, in which the platinum-containing moiety, when conjugated to the analyte-specific binding reagent, does not have covalent binding activity. Methods, compositions, and kits for the production and use of such platinum-conjugated analyte-specific binding reagents are also provided.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Platinum-Conjugated Analyte-Specific Binding Reagents

The present disclosure provides platinum-conjugated binding reagents for use in analyte detection assays. The platinum-conjugated binding reagents provided herein, once generated, do not require covalent binding activity of the platinum-moiety used to generate them to function as analyte detection reagents. Indeed, this activity could negatively impact the use of these binding reagents in analyte detection. For example, a platinum-conjugated analyte-specific binding regent in which the platinum-containing moiety maintained its covalent binding activity (e.g., the covalent binding activity of cisplatin) could react with proteins or other biomolecules on non-target cells, thereby creating false a positive result, and/or react with other binding reagents used in the assay (e.g., in a multiplex assay) and negatively impact their function. Therefore, in contrast to platinum-conjugated antibodies used to deliver cytostatic/cytotoxic forms of cisplatin to a target cancer cell, platinum-conjugated binding reagents according to the present disclosure do not require the use of linkers designed to preserve the covalent binding activity of the platinum-containing moiety used to make them. Thus, in certain embodiments, the covalent binding activity of the platinum moiety can be employed to "directly" conjugate it to a desired binding reagent, e.g., an antibody. Other platinum conjugation methods/reagents may be used that do not maintain the covalent binding activity of the platinum moiety, e.g., the use of linkers or chemistries that eliminate the covalent binding activity of the platinum moiety during conjugation to a binding reagent.

Examples of platinum-containing moieties include, without limitation, cisplatin, carboplatin, oxaliplatin, nedaplatin, lobaplatin, heptaplatin, satraplatin, picoplatin, prolindac, lipoplatin, JM-11, NSC 170898, ormaplatin, sebriplatin, enloplatin, zeniplatin, spiroplatin, cycloplatam, miboplatin, iproplatin, TRK-710, SPI-77, aroplatin, BBR3464, etc. In some embodiments the platinum derivative is cisplatin,

[Pt(NH$_3$)$_2$Cl$_2$]. In many embodiments, the analyte-specific binding reagent is conjugated directly to the platinum-containing moiety, i.e., there is no linker between them (e.g., a polymer linker, e.g., a carboxymethyl dextran linker). For example, an antibody (or other binding reagent) can be prepared for conjugation by treatment with the reducing agent TCEP (tris(2-carboxyethyl)phosphine) to generate free cysteine thiols followed by contacting/incubating it with cisplatin, which covalently binds to free thiols of the reduced antibody/binding reagent. Additional methods for generating directly conjugated binding reagents may be employed.

The platinum atoms present in platinum-containing moieties (sometimes generically referred to as "mass tags") used to generate platinum-conjugated binding reagents may be a naturally occurring mixture of platinum isotopes, or may be enriched for a platinum isotope of interest. Naturally occurring platinum contains six stable isotopes (190, 192, 194, 195, 196, 198), any of which may be enriched. Where multiple platinum isotopes are used, determination of the presence of an analyte can be achieved by detecting/measuring only one isotope, e.g. the most abundant isotope (e.g., Pt$^{195}$). However, the channels occupied by the non-detected isotopes could be used for additional markers, thus providing a benefit for binding reagents enriched for an isotope of interest.

The platinum-containing binding reagents described herein increase the number of analytical channels used in mass cytometry experiments by up to six, i.e., the number of stable platinum isotopes detectable at AM 190, 192, 194, 195, 196, and 198.

As noted above, the specific binding reagent used in the method may be any type of molecule that is capable of specific binding to an analyte (or binding partner). Non-limiting examples of analyte-specific binding reagents include: an antibody, a peptide-MHC tetramer, a nucleic acid (e.g., ssRNA or ssDNA), an aptamer, a ligand specific for a cell surface receptor, etc. Analytes of interest include cytoplasmic, cell surface or secreted biomolecules, frequently biopolymers, e.g. polypeptides, polysaccharides, polynucleotides, lipids, etc. In some embodiments, analytes include specific epitopes. Epitopes are frequently identified using specific monoclonal antibodies or receptor probes. In some cases, the molecular entities comprising the epitope are from two or more substances and comprise a defined structure. Examples include combinatorially determined epitopes associated with heterodimeric proteins. An analyte may be a specifically-modified protein (isoform) or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one analyte while an inactive conformation of a receptor may comprise another, e.g. the active and inactive forms of heterodimeric integrin.

Analytes of interest include biological molecules in a variety of spatial configurations, on a variety of substrates, and in a variety of degraded states. An analyte may be a naturally occurring protein in its native conformation or chemically altered, denatured state. An analyte may be affixed to a cell in its native orientation, or it may be adhered to a variety of substrates, including synthetic substrates e.g. glass, plastic, or metal. An analyte may be affixed to planar substrates or bead-like substrates in a suspension. An analyte may be affixed to a substrate in a particular orientation by a second binding agent, such as an antibody, as in the case of a sandwich ELISA.

Analytes of interest include polypeptides, and the epitope that is being quantitated by be a primary amino acid epitope, an epitope formed by protein secondary or tertiary structure, an epitope formed by two or more interacting polypeptides, or an epitope that results from posttranslational modification of a polypeptide.

Among the post-translational modifications that can be probed, are protein specific glycoslyation. Membrane associated carbohydrate is exclusively in the form of oligosaccharides covalently attached to proteins forming glycoproteins, and to a lesser extent covalently attached to lipid forming the glycolipids. Many proteins are modified at their N-termini following synthesis; in most cases the initiator methionine is hydrolyzed and an acetyl group is added to the new N-terminal amino acid. Post-translational methylation occurs at lysine residues in some proteins. Post-translational phosphorylation is one of the most common protein modifications that occurs in animal cells, often as a transient mechanism to regulate the biological activity of a protein. In animal cells serine, threonine and tyrosine are the amino acids subject to phosphorylation. Sulfate modification of proteins occurs at tyrosine residues such as in fibrinogen and in some secreted proteins. Prenylation refers to the addition of the 15 carbon farnesyl group or the 20 carbon geranylgeranyl group to acceptor proteins, both of which are isoprenoid compounds derived from the cholesterol biosynthetic pathway. Modifications of proteins that depend upon vitamin C as a cofactor include proline and lysine hydroxylations and carboxy terminal amidation. Vitamin K is a cofactor in the carboxylation of glutamic acid residues that results in the formation of a γ-carboxyglutamate (gamma-carboxyglutamate), referred to as a gla residue.

Methods of Use

Methods are provided for detecting the presence of an analyte in a sample using the platinum-conjugated binding reagents disclosed herein. Any convenient method for the detection/measurement of the platinum (or specific platinum isotope) in a platinum-labeled binding reagent may be used. Non-limiting examples are provided below.

In certain embodiments, the method is for detecting an analyte on a particle. In some cases, the particle is a cell. An analyte "on a cell" means that the analyte can be present on the surface of a cell (extracellular), inside a cell (intracellular), or otherwise associated with a cell. The particle being analyzed can be one or more particles in a population of particles, which may be naturally occurring particles, for example a population of cells. A population of cells includes genetically engineered cell lines, cells derived from transgenic animals, etc. of any cell type and size, including bacterial, fungal, plant and animal cells.

Cells for use in the disclosed methods can be an organism, a single cell type derived from an organism, or can be a mixture of cell types. Included are naturally occurring cells and cell populations, genetically engineered cell lines, cells derived from transgenic animals, etc. Virtually any cell type and size can be accommodated. Suitable cells include bacterial, fungal, plant and animal cells. In one embodiment of the invention, the cells are mammalian cells, e.g. complex cell populations such as naturally occurring tissues, for example blood, liver, pancreas, neural tissue, bone marrow, skin, and the like. In another embodiment of the invention, the cells are from diseased origin, such as solid tumors or leukemia. Some tissues may be disrupted into a monodispersed suspension if the cells are not yet already in suspension. Alternatively, the cells may be a cultured population, e.g. a culture derived from a complex population, a culture derived from a single cell type where the cells have differentiated into multiple lineages, or where the cells are responding differentially to stimulus, and the like.

Cell types that can be employed in the disclosed methods include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells;, etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells can be transformed or neoplastic cells of different types, e.g. carcinomas of different cell origins, lymphomas of different cell types, etc. The American Type Culture Collection (Manassas, Va.) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) *Journal of Cellular Biochemistry*, Supplement 24:32-91). Included are different cell lines derived spontaneously, or selected for desired growth or response characteristics from an individual cell line; and may include multiple cell lines derived from a similar tumor type but from distinct patients or sites.

Cells may be non-adherent, e.g. blood cells including monocytes, T cells, B-cells; tumor cells, etc., or adherent cells, e.g. epithelial cells, endothelial cells, neural cells, etc. In embodiments in which cells need to be in suspension for analysis (e.g., mass cytometry), normally adherent cells can be dissociated from the substrate that they are adhered to, and from other cells, in a manner that maintains their ability to recognize and bind to probe molecules.

Cells can be acquired from an individual using, e.g., a draw, a lavage, a wash, surgical dissection etc., from a variety of tissues, e.g., blood, marrow, a solid tissue (e.g., a solid tumor), ascites, by a variety of techniques that are known in the art. Cells may be obtained from fixed or unfixed, fresh or frozen, whole or disaggregated samples. Disaggregation of tissue may occur either mechanically or enzymatically using known, or future, techniques.

In certain embodiments, the cells are enriched, separated or purified prior to analysis/contacting with the platinum-conjugated binding reagents described herein. Various methods and devices exist for pre-separating component parts of the sample. These methods include filters, centrifuges, chromatographs, and other well-known fluid separation methods; gross separation using columns, centrifuges, filters, separation by killing of unwanted cells, separation with fluorescence activated cell sorters, separation by directly or indirectly binding cells to a ligand immobilized on a physical support, such as panning techniques, separation by column immunoadsorption, and separation using magnetic immunobeads.

As discussed elsewhere herein, cellular analytes of interest may be located on the cell surface, or may be located in the cytoplasm or nucleus of the cell. For such intracellular labeling it is generally desirable to permeabilize and/or fix the cells. For example, where transient signaling pathways are being analyzed, it is desirable to fix the cells at the desired time point, then permeabilize them to allow the binding reagent(s) specific for intracellular analytes of interest access to the intracellular environment. Various fixatives are known in the art, including formaldehyde, paraformaldehyde, formaldehyde/acetone, methanol/acetone, etc. Paraformaldehyde used at a final concentration of about 1 to 2% has been found to be a good cross-linking fixative. Permeabilizing agents are known in the art, and include mild detergents, such as Triton X-100, NP-40, saponin, etc.; methanol, and the like. It may also be desirable to label cells with a positive heavy metal control, e.g. a DNA intercalator labeled with a heavy metal, e.g. iridium, etc. It is noted here, that in some embodiments, both intracellular and extracellular analytes are detected simultaneously in an assay.

The presence of platinum, and optionally other elemental labels, associated with a particle is detected by elemental analysis. As used herein, the term "elemental analysis" refers to a method by which the presence and/or abundance of elements of a sample are evaluated. "Capacitively coupled plasma" (CCP) means a source of ionization in which a plasma is established by capacitive coupling of radiofrequency energy at atmospheric pressure or at a reduced pressure (typically between 1 and 500 Torr) in a graphite or quartz tube. The term "inductively coupled plasma" (ICP) means a source of atomization and ionization in which a plasma is established in an inert gas (usually argon) by the inductive coupling of radiofrequency energy. The frequency of excitation force is in the MHz range. The term "plasma source" means a source of atoms or atomic ions comprising a hot gas (usually argon) in which there are approximately equal numbers of electrons and ions, and in which the Debye length is small relative to the dimensions of the source. The term "flow cell" refers to a conduit in which particles flow, in a medium, one by one in single file. The term "a diverter" refers to a branch of a flow cell in which particles can be separated from other components passing through the flow cell. "Laser ablation" means a source of combusted material liberated from an otherwise intact surface by exposure to laser radiation, optionally used in conjunction with microscopy to preserve spatial information. "Mass spectrometer" means an instrument for producing ions in a gas and analyzing them according to their mass/charge ratio. "Microwave induced plasma" (MIP) means a source of atomization and ionization in which a plasma is established in an inert gas (typically nitrogen, argon or helium) by the coupling of microwave energy. The frequency of excitation force is in the GHz range. "Glow discharge" (GD) means a source of ionization in which a discharge is established in a low pressure gas (typically between 0.01 and 10 Torr), typically argon, nitrogen or air, by a direct current (or less commonly radiofrequency) potential between electrodes. "Graphite furnace" means a spectrometer system that includes a vaporization and atomization source comprised of a heated graphite tube. Spectroscopic detection of elements within the furnace may be performed by optical absorption or emission, or the sample may be transported from the furnace to a plasma source (e.g. inductively coupled plasma) for excitation and determination by optical or mass spectrometry. In some embodiments the methods for analysis utilize ICP-MS. In some embodiments the ICP-MS is performed with solution analysis, for example ELAN DRC II, Perkin-Elmer. Alternatively the analysis is performed by an elemental analysis-driven imaging system (e.g. laser ablation ICP-MS). Devices for such analytic methods are known in the art.

In other embodiments the analysis is performed with a mass cytometer (e.g. CyTOF, DVS Sciences/Fluidigm Sciences; South San Francisco, Calif.) in which particles are introduced into a fluidic system and introduced into the mass cytometer one particle at a time. In one embodiment, particles are carried in a liquid suspension and sprayed into a plasma source by means of a nebulizer. In another embodiment, the particles may be hydrodynamically focused one particle at a time through a flow cell using a sheath fluid. In particular embodiments, the particles may be compartmentalized in the flow cell by introduction of an immiscible barrier, e.g., using a gas (e.g., air or nitrogen) or oil, such that the particle is physically separated from other particles that are passing through the flow cell. The particles may be compartmentalized prior to or during introduction of the particle into the flow cell by introducing an immiscible material (e.g., air or oil) into the flow path.

The general principles of mass cytometry, including methods by which single cell/particle suspensions can be made, methods by which particles can be labeled, methods for atomizing particles and methods for performing elemental analysis on particles, as well as hardware that can be employed in mass cytometry, including flow cells, ionization chambers, reagents, mass spectrometers and computer control systems are known and are reviewed in a variety of publications including, but not limited to Bandura et al Analytical Chemistry 2009 81 6813-6822), Tanner et al (Pure Appl. Chem 2008 80: 2627-2641), U.S. Pat. No. 7,479,630 (Method and apparatus for flow cytometry linked with elemental analysis) and U.S. Pat. No. 7,135,296 (Elemental analysis of tagged biologically active materials); and published U.S. patent application 20080046194, for example, which publications are incorporated by reference herein for disclosure of those methods and hardware.

A database of analytic information can be compiled. These databases may include results from known cell types, references from the analysis of cells treated under particular conditions, and the like. A data matrix may be generated, where each point of the data matrix corresponds to a readout from a cell, where data for each cell may comprise readouts from multiple mass tag labels. The readout may be a mean, median or the variance or other statistically or mathematically derived value associated with the measurement. The output readout information may be further refined by direct comparison with the corresponding reference readout. The absolute values obtained for each output under identical conditions will display a variability that is inherent in live biological systems and also reflects individual cellular variability as well as the variability inherent between individuals.

The method described above may be multiplexed in that the assay can be done using multiple analyte-specific binding reagents each of which is specific for a different analyte (e.g., more than 2 specific binding reagents, up to 5 specific binding reagents, up to 10 specific binding reagents, up to 20 specific binding reagents, up to 50 specific binding reagents or up to 100 specific binding reagents or more). Each specific binding reagent may be linked to a different mass tag so as to be distinguishable from all other specific binding reagents used in the multiplex assay, e.g., when detected by mass cytometry. Alternatively or in addition, multiplexing may involve using labels that are not mass tags, e.g., fluorescent labels.

In any embodiment, data can be forwarded to a "remote location", where "remote location," means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the image may be analyzed by an MD or other qualified medical professional, and a report based on the results of the analysis of the image may be forwarded to the patient from which the sample was obtained.

In some cases, the method may be employed in a variety of diagnostic, drug discovery, and research applications that include, but are not limited to, diagnosis or monitoring of a disease or condition (where the image identifies a marker for the disease or condition), discovery of drug targets (where the a marker in the image may be targeted for drug therapy), drug screening (where the effects of a drug are monitored by a marker shown in the image), determining drug susceptibility (where drug susceptibility is associated with a marker) and basic research (where is it desirable to measure the differences between cells in a sample).

In certain embodiments, two different samples may be compared using the above methods. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell.

In certain embodiments, the disclosed analyte-specific binding reagents find use in methods for isolating (or sorting) a particle based on the presence, level, or absence of one or more analyte of interest.

In one example of such methods, a particle is labeled using an analyte-specific binding reagent that is cleavably linked to an elemental tag (e.g., a platinum moiety), the labeled particle is passed through a flow cell of a mass cytometer, the elemental tag is cleaved from the labeled particle in a controlled fashion, elemental analysis of the cleaved elemental tag is performed without destroying the particle to produce data, the data for the particle is matched with the particle, and the particle is collected based on the data. (See, e.g., United States Patent Application Publication No. US 20120077714 entitled "Mass spectrometry based particle separation", hereby incorporated by reference herein).

In another embodiment, a platinum moiety-specific antibody is used as an affinity reagent to isolate/purify a particle having an analyte of interest associated therewith. In such embodiments, a platinum moiety-conjugated analyte-specific binding reagent is bound to an analyte on a particle through analyte-specific binding (e.g., by contacting the particle and the binding reagent under analyte binding conditions) after which the binding reagent-bound particle is contacted with an antibody specific for the platinum moiety conjugated to the binding reagent under appropriate binding conditions. Particles to which the platinum moiety-specific antibody is bound can be isolated in any convenient manner. For example, the platinum moiety-specific antibody can be bound, either covalently or non-covalently (e.g., via a binding pair interaction), to a solid substrate (e.g., a bead or a surface). Analyte containing particles will bind to the substrate via the binding interaction between the platinum moiety on the analyte-specific binding reagent and the platinum moiety-specific antibody while non-analyte containing particles will not. Particles bound to the substrate can then be harvested as desired, e.g., using MACS, filtration, centrifugation, or any other convenient method.

As another example, a particle that is bound to a platinum-conjugated analyte specific binding reagent can be further labeled with a fluorescent tag which can be used to sort the particle using flow cytometry. The fluorescent tag can be covalently bound to the platinum-conjugated analyte specific binding reagent or can be non-covalently bound to the platinum-conjugated analyte specific binding reagent, e.g., via a binding pair in which one member of the binging pair is labeled with a fluorescent tag and the other member of the binding pair is conjugated to, or is inherently part of, the analyte specific binding reagent. For example, a platinum moiety-specific antibody labeled with a fluorescent tag (or other detectable tag) can be contacted with particles (containing at least one particle having the analyte of interest) and a platinum moiety-conjugated analyte specific binding reagent under appropriate binding conditions, either sequentially or simultaneously. Particles having the analyte will bind to the platinum moiety-conjugated analyte specific binding reagent which in turn will bind the fluorescently tagged platinum-moiety specific antibody and thus be fluorescently labeled. Such particles can be sorted/isolated by flow cytometry.

In certain embodiments, the disclosed analyte-specific binding reagents find use in methods for detecting soluble analytes. In one example, a capture beads specific for a soluble analyte of interest (e.g., having an analyte specific antibody or sequence specific oligonucleotide bound thereto) is contacted with a soluble sample containing or suspected of containing the analyte (e.g., blood sample, serum sample, cell culture supernatant, etc.) under analyte binding conditions. The capture bead is then contacted with an analyte specific platinum moiety-conjugated binding reagent under appropriate binding conditions. In such assays, the binding site for the capture bead and the analyte-specific platinum moiety conjugated binding reagent for the soluble analyte are different and do not interfere with one another. The bead(s) can then be analyzed by mass cytometry to determine the presence of and/or quantitate the amount of the soluble analyte in the sample.

In certain embodiments, a platinum moiety can be conjugated to a substrate for an enzyme and used to detect the presence of the enzyme activity in a sample, e.g., a biological fluid. (See, e.g., PCT Application Publication No. WO 2015077884 entitled "Multiplex enzyme assay using elemental analysis", hereby incorporated by reference herein). For example, the method can include: (i) attaching an elementally-coded bead to a first amino acid of a peptide substrate to form an immobilized peptide substrate, the peptide substrate having a first amino acid and a last amino acid and being a substrate for an enzyme (e.g., a protease); (ii) attaching a platinum moiety between the substrate for the enzyme and the last amino acid, or on the last amino acid, to form a tagged peptide substrate; (iii) incubating the immobilized, tagged peptide substrate with the biological fluid; and (iv) detecting the platinum moiety and the elementally-coded bead in the biological fluid by elemental analysis.

Kits

Also provided by the present disclosure are kits for practicing the method as described above. The subject kit is configured to enable a user to perform an analyte detection method described herein and include an analyte-specific binding reagent conjugated to a platinum-containing moiety, where the platinum-containing moiety does not have covalent binding activity. In some embodiments, the binding reagent is an antibody conjugated with cisplatin. The platinum content of the binding reagent may be naturally occurring or synthetically enriched for an isotope of interest. Also included may be buffers, controls, and the like. For example, the kit may also contain a reference sample to which results obtained from a test sample may be compared.

In other embodiments, the kit includes reagents sufficient to conjugate a platinum-containing moiety with a binding reagent. In some embodiments, the kit contains a reducing agent (e.g., tris(2-carboxyethyl)phosphine (TCEP)) and a covalent binding agent that contains platinum, e.g., cisplatin.

In addition to above-mentioned components, the subject kit may further include instructions for using the components of the kit to practice the methods described herein. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to above-mentioned components, the subject kit may include software to perform comparison of data.

In order to further illustrate the present invention, the following specific examples are given with the understanding that they are being offered to illustrate the present invention and should not be construed in any way as limiting its scope.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Cisplatin, or cis-diamminedichloroplatinum(II) is a cytostatic agent frequently used in the treatment of various cancers (17-19). While its main mechanism of action is considered to be covalent binding to and thereby inhibiting the function of DNA in tumor cells (20), it also can bind to the glycosaminoglycan hyaluronan (21), or to proteins via reactions with thiols (22-26). Indeed, most cisplatin binds to serum protein within hours after injection into patients (27). Cisplatin can be physically linked to Ab (28-30) or avidin (31) via dextran linkers, or embedded in Ab-decorated nanoparticles (32, 33) or liposomes (34), with the aim to achieve target-specific delivery of cisplatin in cancer patients where it can act as a cytostatic/cytotoxic agent. As preserving the covalent binding activity of cisplatin in these conjugates is necessary for their intended purpose, the linkers employed in these antibody conjugates are specifically designed to not interfere with the this activity.

Cisplatin has also been used directly as a viability reagent in cell analysis assays. In this context, cisplatin is contacted to a cell sample in which it selectively crosses the plasma membrane of non-viable cells and covalently modifies a biological macromolecule within the cell. Similar to the cytotoxic/cytostatic use of cisplatin described above, the ability of cisplatin to bind covalently with biomolecules is required for its use as a viability reagent. (See, e.g., US Patent Application Publication No. US 20140329272 for a description of the use of cisplatin as a viability reagent, hereby incorporated by reference herein in its entirety.)

In the experiments described below, the direct labeling of monoclonal Abs with platinum (in the form of cisplatin) for mass cytometric analysis is described. As noted elsewhere herein, direct cisplatin conjugation of Ab (or other binding reagents) circumvents the use of polymer linkers and has the potential to increase the number of analytical channels used in mass cytometry experiment by up to six, i.e., the number of stable platinum isotopes detectable at AM 190, 192, 194, 195, 196, and 198.

These binding reagent platinum conjugates were tested in surface, intracellular, and phospho-epitope-specific immune phenotyping applications.

Materials and Methods

Reagents

Millipore filtered deionized water ("water") was used as sample carrier and to prepare 1x PBS from 10x PBS (Rockland, Gilbertsville, PA) and CyPBS/0.1% BSA (Sigma, St. Louis, Mo.) ("CyPBS/BSA") buffer that was used as staining and washing media for PBMC. Buffers were filtered over 0.22 μm membranes (EMD Millipore, Billerica, Mass.). Unlabeled, carrier protein-free Ab (Table SI) were purchased from Tonbo Biosciences (San Diego, Calif.), Southern Biotech (Birmingham, Ala.), eBioscience (San Diego, Calif.), Biolegend (San Diego, Calif.), BD Biosciences (San Jose, Calif.), Santa Cruz Biotechnology (Dallas, Tex.), abcam (Cambridge, Mass.) or Sanquin (Amsterdam, The Netherlands). In-house Ab conjugations with lanthanide isotopes were carried out using MAXPAR® kits (Fluidigm, Sunnyvale, Calif.) according to the manufacturer's instructions. Natural abundance cisplatin was purchased from Enzo (Farmingdale, N.Y.), dissolved in dimethylsulfoxide (DMSO; Sigma) to 100 mM, and stored at −80° C. Cisplatin containing isotopically enriched Pt194 and Pt198 was purchased from Fluidigm Sciences (South San Francisco, Calif.) as 1 mM solution in DMSO that were kept at −20° C. according to the manufacturer's instructions. Highly isotopically-enriched metal salts not available through Fluidigm were purchased from Trace Sciences (Richmond Hill, ON, Canada): Pd104, Pd106, Pd108, Pd110, In113, In115, Dy163, Gd155, or from Sigma: Pr141. Ab were diluted to working concentrations in CyPBS/BSA and filtered through 0.1 μm spin filters (Amicon, Millipore, Billerica, Mass.). mDOTA was loaded with natural abundance Indium (Sigma) according to a previously published protocol (6). Labeling of CD45 Ab with Palladium isotopes was carried out as described (13).

Sample and Specimen Description

Peripheral blood mononuclear cells (PBMC) were prepared from TrimaAccel® leukoreduction system (LRS) chamber content (Terumo BCT, Lakewood, Colo.) obtained from the Stanford Blood Center under the IRB # 5136, by gradient centrifugation over Ficoll medium (GE Healthcare, Uppsala, Sweden), washed and cryopreserved according to standard procedures (see the website at "http:" followed by "//iti.stanford.edu/content/dam/sm/iti/documents/himc/pro-tocols/SOP-PBMCDirectFicollHeparinv1-4-1.pdf"). Frozen PBMC were kept in vapor phase liquid nitrogen for longer-term storage. For experiments, PBMC samples were thawed in a 37° C. water bath and washed twice in RPMI 1640 (HyClone®, Thermo Scientific, Waltham, Mass.) supplemented with 10% FBS (Atlanta Biologicals, Flowery Branch, Ga.) in 15 or 50 mL Falcon tubes (BD Biosciences) containing penicillin, streptomycin, and 10 U/mL benzonase (Sigma), resuspended in PBS, and kept on ice for further use. PBMC were counted and checked for viability using a Vicell counter (Beckman Coulter, Brea, Calif.). PBMC viability was typically >95%, except for experiments in which isolated PBMC were rested in PBS/0.1% BSA buffer overnight at 4° C. in order to achieve an increased frequency of dead cells.

Platinum Labeling of Antibody

Carrier-protein-free Ab were prepared for conjugation as described in the MAXPAR® labeling protocol (Fluidigm Sciences): 50 μg Ab was diluted or reconstituted in R buffer (Fluidigm) to achieve an Ab solution of at least 50% v/v R buffer. The Ab was concentrated using a 30 kDa spin filter (EMD Millipore, Billerica, Mass.). 100 μL of a 4 mM tris(2-carboxyethyl)phosphine (TCEP) solution (Thermo, Waltham, Mass.) diluted in R buffer from a 500 mM stock solution was added to the Ab, mixed by pipetting, and incubated in the spin column for 30 min in a 37° C. water bath. Ab were washed twice, with 300 μL and 400 μL C buffer (Fluidigm Sciences), respectively. 20 nmol (20 μL of a 1 mM solution in DMSO) cisplatin was thawed and added to the Ab, mixed by pipetting and incubated for 60-90 min in a 37° C. water bath, analogous to the MAXPAR® procedure. The amount of cisplatin used was guided by the approx. 20 nmol of polymer used in one reaction of a MAXPAR® labeling kit. The utility of that concentration was confirmed by a respective titration experiment (FIG. 1C). The presence of DMSO serving as a solvent of cisplatin was limited to 2% v/v in the conjugation reaction, by adjusting the volume of the Ab solution using C buffer prior to the addition of cisplatin. In some cases e.g. for the aforementioned titration experiment, reaction volumes of were greater than 400 μL and required the labeling to be performed in a 1.6 mL microcentrifuge tube, not on the column, without apparent differences for the resulting conjugate. Labeling of Ab with isotopically purified cisplatins (concentration, 1 mmol) was performed in total volume of 1mL in a 1.6 mL microcentrifuge tube. All other labeling reactions (e.g. with natural abundance cisplatin, 100 mmol concetration) were performed on the column in a volume of up to 200 µL. After conjugation, the conjugates were washed three times with 300 µL W buffer (Fluidigm) over a 30 kDa spin filter for 10 min at 4° C. and 17,500×g, then transferred to a 1.6 mL microcentrifuge tube. Protein concentration was quantified by Nanodrop (Thermo Fisher, Waltham, Mass., USA) at 280 nm and PBS-based Ab stabilizer (Candor Biosciences, Wangen, Germany) was added to the Ab preparation to a final concentration of 50%. Ab were kept at 4° C.

Barcoding and Immunophenotyping of PBMC

The barcoding experiment was carried out as described before (13) using the indicated Pt- and Pd-labeled CD45 conjugates. To simulate different samples prior to CD45-barcoding, $1\times10^6$ cell fractions of a single, $20\times10^6$ PBMC sample were manipulated in vitro by overnight incubation with a B cell depleting Ab (rituximab, Roche, Grenzach-Wyhlen, Germany) at 37° C., by a 30 min incubation with PMA/ionomycin at 37° C. (both Sigma), by adding unlabeled CD8 Ab for 20 min on ice (final concentration 50 µg/mL, clone SK1, Biolegend, San Diego, Calif.), or combinations thereof. Boolean deconvolution of data was performed as described (13), using FlowJo X.0.7. Deconvoluted data were analyzed for effects expected from the in vitro treatments, i.e. B cell depletion, upregulation of CD11c by NK cells (35) and inhibition of CD8 staining.

Mass Cytometry

Mass cytometry measurements were performed on a CyTOF 2 instrument (Fluidigm Sciences; South San Francisco, Calif.), unless otherwise indicated. Cells were injected as a single-cell suspension in water supplemented with EQ™ Four element calibration beads (Fluidigm Sciences) after filtration through a 35 µm nylon mesh (cell strainer cap tubes, BD, San Jose, Calif.) immediately prior to acquisition. Calibration bead signals were used to monitor the detector performance over the runtime. All comparisons were made between data acquired closely in time, from measurements lasting usually less than 10 min; therefore, the data was not normalized using the calibration beads.

The CyTOF 2 instrument was started, tuned, and cleaned as per manufacturer's instructions. QC was performed based on collecting information of the automated tuning procedure and data of Europium beads (Fluidigm Sciences) for event recovery, signals elicited by the beads at AM 151 and 153 as well as for the frequency of bead-bead doublet events, and successfully passed for all experiments. CyTOF 2 data were acquired in Di 'instrument' calibration mode, with noise reduction turned on and lower and upper cell length parameter values set to 10 and 150, respectively. FCS files were generated by CyTOF® instrument control software v6.0.622 (Fluidigm Sciences), which also served to control the instrument.

When used, the CyTOF version 1 instrument was started up, prepared and operated as described before (13, 36). Data were acquired in Dd 'internal' calibration mode, with noise reduction turned off and lower and upper cell length parameter values set to 10 and 75, respectively. FCS files were generated by CyTOF® instrument control software v5.1.602 (Fluidigm Sciences), which also served to control the instrument.

Capture Bead Assay

Signals elicited by various Ab-metal-conjugates on the CyTOF mass cytometer were determined as follows: aliquots of 20 µL anti-mouse kappa light chain Ab capture bead solution (COMP beads; BD Biosciences, San Jose, Calif.) were pelleted for 10 min at 800 g in 96-well V-bottom plates (Corning, Corning, N.Y.). Beads were resuspended with 40 µL of various 1 µg/mL Ab solutions diluted in PBS/BSA and incubated for 1 h on ice. Beads were washed twice with 200 µL PBS/BSA, were pooled and pelleted in suitable combinations. Then, beads were washed twice in 500 µL water, resuspended in water containing EQ 4 element beads (Fluidigm Sciences), filtered over a 35 µm mesh and acquired on a CyTOF version 1 (Fluidigm Sciences). Data were exported from CyTOF software to FCS files using a lower convolution threshold value of 3.

Capture beads were identified by signals detected in the expected AM channels (the mass channels occupied by Ab-metal-conjugates tested), after securing the absence of cells by gating on Ir193/Ir191-negative events, and excluding EQ 4 element by gating on Lu-175/Ce-140—negative events. Capture beads representing single stainings were deconvoluted by Boolean gating as used before to extract cell samples from CD45-barcoded sample convolutes (13). Median signal intensities of capture bead populations were determined.

Determination of Metal Ions Per Ab Molecule

Ab-lanthanide-conjugates were made in-house according to the MAXPAR® protocol or purchased from Fluidigm Sciences and diluted at a final v/v ratio of 1:100,000 in tuning solution (Fluidigm Sciences). Samples were injected into a CyTOF version 1 and signals (duals counts) were monitored over time until they stabilized. Data was recorded (1, step value; settling time, 20 ms; 78,600 pushes per reading). Average dual count values from at least 20 subsequent readings were used. The number of ions associated with one Ab molecule was determined using tuning solution as a standard and the dual count value resulting from the Ab conjugate measurement, the Ab conjugate concentration, the dilution of the Ab conjugate and the MW of Ab (150 kDa).

A similar procedure was performed for Pt-conjugated Ab described in here, using 2% ICP-MS grade HCl as a matrix for 1:10,000-fold dilutions of Pt conjugates and natural abundance Pt ICP-MS solution diluted in 2% HCL to 0.5 ppb as a standard (both Spex CertiPrep, Metuchen, N.J.).

Cytotoxicity of Pt-Ab-conjugates

The cytotoxicity of Pt-Ab-conjugates was analyzed at the level of the viability of PBMC that were incubated for up to one week at 37° C. in a humid atmosphere incubator with Pt-labeled CD45 mAb in RPMI1640 (HyClone; Thermo Scientific, Waltham, Mass.) supplemented with 10% FBS (Atlanta Biologicals, Flowery Branch, Ga.), penicillin, streptomycin and glutamine (Sigma-Aldrich). PBMC viability was analyzed using the Vicell counter (Beckman Coulter, Brea, Calif.).

Equal numbers of PBMC were seeded into cavities of a 96-well plate in the presence or absence of 5 µg/mL Pt194- or Pt198-labeled CD45 mAb or one of the following controls: unlabeled CD45 Ab (Biolegend, 5 µg/mL), PeCy7-labeled CD45 Ab (Biolegend, 5 µg/mL), In113-labeled CD45 Ab (in-house, 5 µg/mL), Sm154-labeled CD45 (Fluidigm Sciences, 1:100 v/v), Pd104-labeled CD45 Ab (in-house, 5 µg/mL), Pd108-labeled CD45 Ab (in-house, 5 µg/mL). Multiple replicates of each condition were prepared and subjected to viability testing at different time points. Reference cell viability in the absence of any Ab at the start of the experiment was determined in quintuplicate, and in duplicate for the subsequent time points, the average of which was used for the graph in FIG. 3B.

Data Analysis and Presentation

FlowJo software (v. X. 0.7, Treestar, OR) was used to analyze and display data, with default settings for CyTOF data ("arcsinh" scaling, axis range between −5 and 12,000). For the analysis of cells, signal intensities were expressed as geometric mean signal intensities (gMSI), thus avoiding the handling of near-zero median values such as in cases were less than 50% of the events of a given population of interest show a signal greater than zero in a particular channel.

Figure 5:
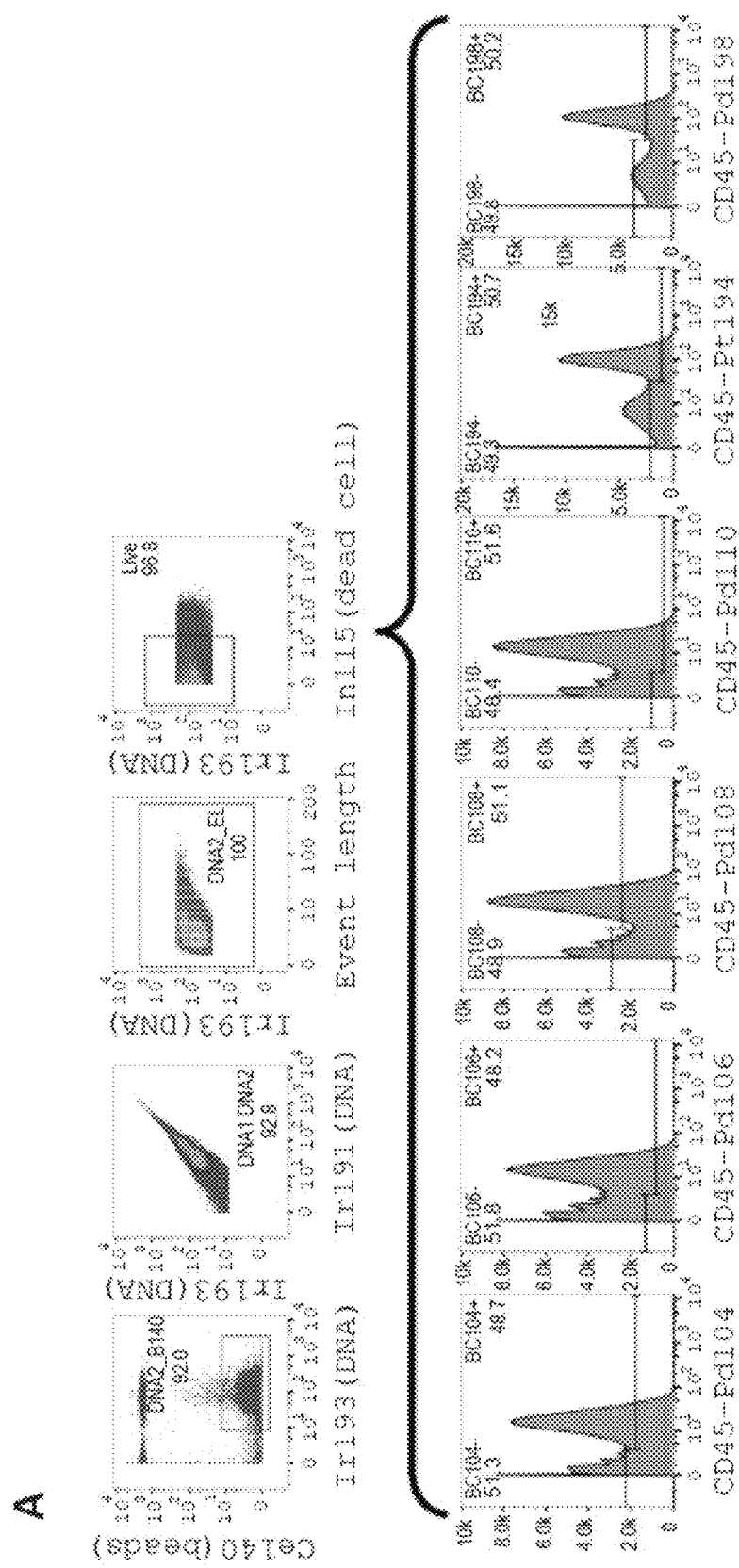
FIG. 5, Panels A-B. Gating strategy in the CD45 barcoding experiment in FIG. 4. (Panel A) Data of the pooled sample were pre-gated as shown, according to Ce140 signal to exclude beads, according to DNA signal, and gating on live cells. No restriction was applied to cell length. Among pre-gated cells, gates were set according to bimodal distribution in CD45 barcoding channels, which served to generate Boolean gates, as described (13). (Panel B) Effects of B cell depletion were studied by quantifying CD19+HLA-DR+B cells as a percentage of parent population, CD8 blockade by quantifying CD8+CD4− T cells as a percentage of parent CD3+ population, and PMA/ionomycin stimulation by the change in CD11c expression on NK cells.
Figure 5:
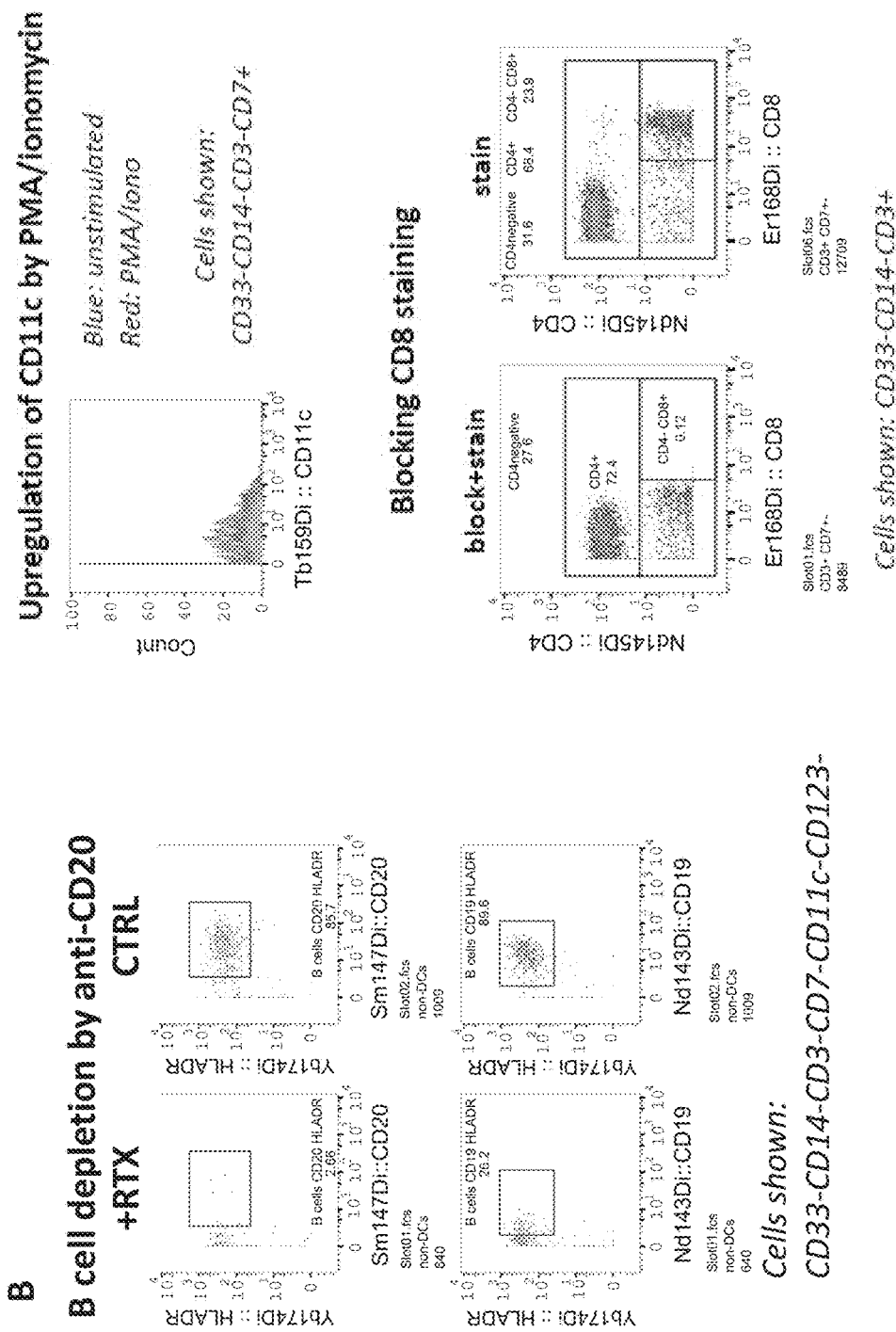

Data from barcoded composite samples were pre-gated according to bead exclusion, DNA detection, cell length restriction, and dead cell exclusion, and deconvoluted using a Boolean gating strategy based on bivariate distribution of cells over signal intensities of CD45 staining used for barcoding (FIG. 5A), as described before (13). Deconvoluted data of CD45+ PBMC were exported from FlowJo and re-imported as single files for further analysis, or imported into Cytobank (www.cytobank.org) (37) for the generation of SPADE trees (38).

Results

Pt-labeling of Antibodies

For cisplatin labeling, carrier protein-free Ab were washed and concentrated on a 30 kDa spin filter, and reduced with tris(2-carboxyethyl)phosphine (TCEP) for 30 min at 37° C. to generate free thiol groups, washed and mixed with cisplatin (FIG. 1A). After one hour co-incubation at 37° C., Ab-cisplatin conjugates were washed to remove unbound cisplatin, quantified by Nanodrop and supplemented with Ab stabilizer.

The 20 nmol of cisplatin used for labeling 50 µg anti-CD8 Ab was sufficient to associate enough metal to the Ab so that $CD8^+$ T cells appeared as well separated in dot plot or histogram representations, based on the signal intensity of the most abundant platinum isotope of natural abundance platinum, Pt195 (FIG. 1B). 20 nmol of cisplatin appeared to saturate most available binding sites on the CD8 Ab under chosen conditions, since increasing the amount of cisplatin in the labeling reaction up to 25-fold did not translate into a proportionately stronger signal (FIG. 1B). Five-fold increased cisplatin amount (100 nmol) did not lead to an equivalent increase in the signal intensity of CD8-Pt* (*, natural abundance) stained cells. The geometric mean signal intensity (geoMSI) of CD8-Pt* was 1.2-fold increased among CD4− T cells, and background staining of CD8-Pt* shown by $CD4^+$ T cells, B cells and monocytes were similarly increased by the 1.3-fold, 1.3-fold and 1.2-fold, respectively. As a five-fold lower amount of cisplatin (4 nmol) led to a decreased signal intensity of the CD8 staining, 20 nmol was considered as optimal among the conditions tested.

The Ab reduction step with TCEP was essential for achieving sufficient signal intensity, as omitting the reduction decreased the CD8 signal intensity in CD4− T cells to 11% of that of the reduced Ab (FIG. 1C). Thus, most, but not all, cisplatin reacts to free thiols of the CD8 Ab, and other linkage pathways play a minor role for the described labeling procedure. Cisplatin reacted to an irrelevant control protein, BSA, using the above protocol, showed no significant binding to PBMC (FIG. 1C). GeoMSI were <0.1 for T and B cells as a well as monocytes. This confirms that binding of cisplatin-Ab-conjugates to PBMC is due to the Ab and not due to cisplatin itself.

Next, CD45 Abs were conjugated to cisplatin containing isotopically-enriched Pt194 or Pt198. As expected, these conjugates stained virtually all PBMC. The geoMSI were greater than 100 for CD45-Pt194 and CD45-Pt198 stained cells (FIG. 1D), similar to Pd-conjugated CD45 Abs (13). The specificity of CD45-Pt194 and CD45-Pt198 was maintained after cisplatin labeling as demonstrated by blocking of the staining reaction by 10-fold concentration of unlabeled CD45 Ab prior to incubation with labeled CD45 Ab. Pt194- and Pt198-conjugates minimally contributed to mutual background signals, presumably by isotopic impurity of Pt194 and Pt198.

PBMC not stained with platinum conjugates showed no relevant signal at AM194 and AM198, indicating that, as expected, biological Pt background is below the CyTOF's detection limit. This confirms the potential utility of Pt-Ab conjugates in mass cytometry immunophenotyping experiments.

The possibility that cisplatin-conjugated Ab still has the capacity of unconjugated cisplatin to act as a dead cell staining reagent was excluded, since in a PBMC sample with a high frequency of dead cells, dead cells identified by high maleimide-DOTA-In* staining signals did not show increased staining intensity resulting from a CD45-Pt194 or CD45-Pt198 Ab (data not shown).

Figure 2:
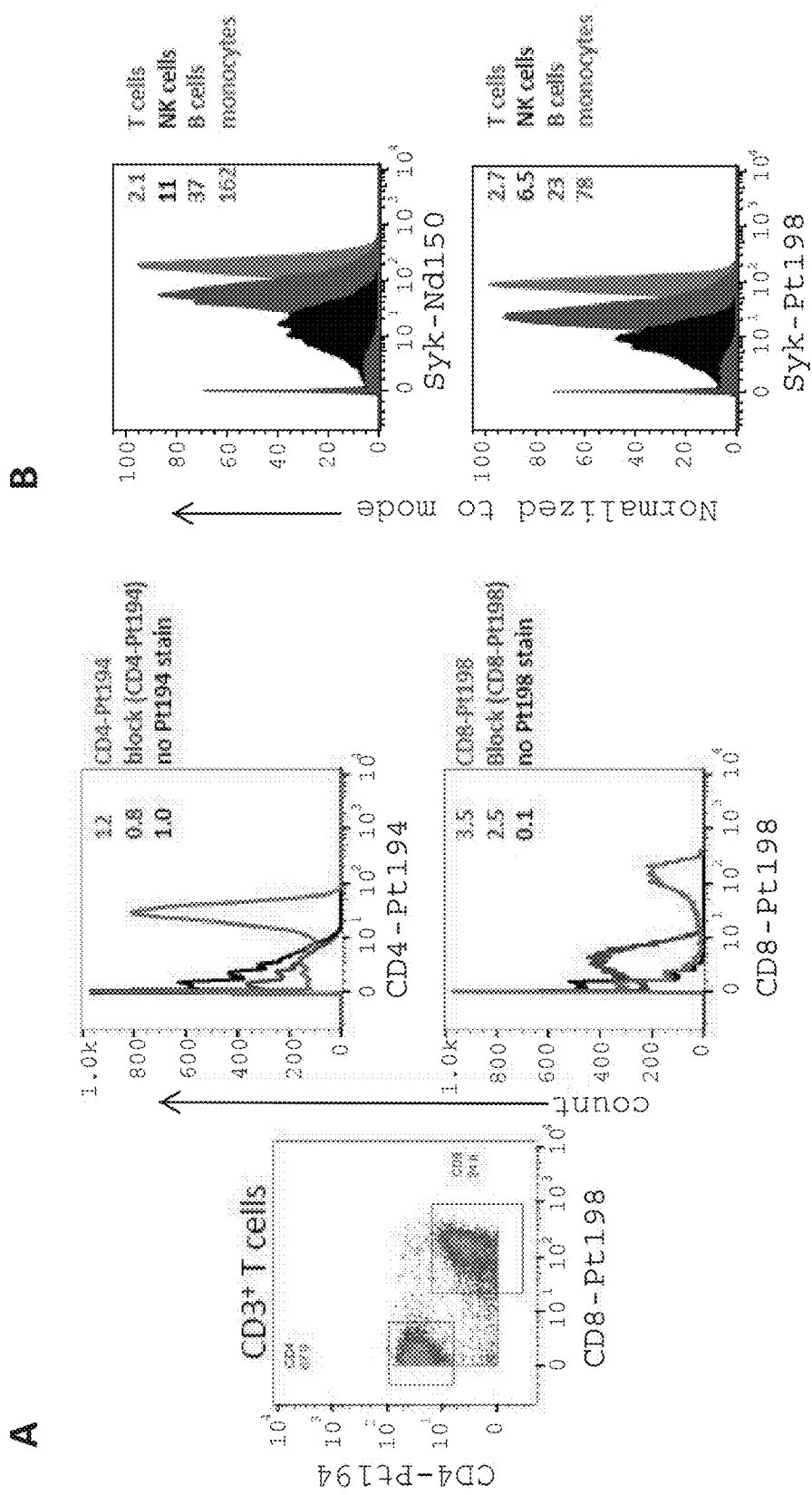
FIG. 2, Panels A-C. Cisplatin-Ab conjugates compare to lanthanide loaded polymer Ab conjugates. (Panel A) PBMC were labeled with CD4-Pt194 and CD8-Pt198 as well as several lineage markers used to distinguish T cells. CD4+ and CD8+ T cells are separated from background and each other. Omitting the Ab staining or blocking the binding of labeled Ab by pre-incubation with unlabeled Ab inhibited the staining. (Panel B) Syk Ab was separately conjugated to Nd150 and Pt198, and both conjugates were used to stain aliquots of the same PBMC sample, along with a lineage marker Ab cocktail. The distribution of Syk expression across major PBMC subsets is revealed by both the Nd150 and the Pt198 conjugate. Numbers in (A)-(B) reflect geoMSI. (Panel C) In-house Pt198-conjugated anti-p-p38 [T180/Y182] (clone 36/p38) was compared to anti-p-p38 [T180/Y182] (clone D3F9) labeled to Gd156 in a PBMC stimulation experiment involving 15 min co-incubation of PBMC with PBS (unstimulated control), TNF-α, IL-6, PMA/ionomycin, IL-21, IL-1, GM-CSF, vanadate alone and a PI/vanadate/IL-21/IL-6 cocktail. After stimulation, samples were fixed with PFA, CD45-barcoded using a 2-of-5 scheme, and further processed as pooled samples. One of two replicates was stained with p-p38-Gd156, the other with p-p38-Pt198. After data acquisition, data was pre-gated and deconvoluted in FlowJo, exported into new FCS files and transferred to Cytobank for SPADE analysis using default settings: 200 target nodes, and downsampling set to 10% of all events to use one tenth of the data for the SPADE analysis, and marking the unstimulated control sample as the "control". SPADE trees of PMA/ionomycin, IL-1 and PBS control stimulation are shown. Clustering was based on CD3, CD19, CD20, CD33, CD14, CD16, CD56, CD4, and CD8 and graphs were colored according to the fold-change of p-p38 signal. Annotations in the upper right SPADE plot apply to all SPADE plots in FIG. 2, Panel C. GeoMSI values differed between p-p38-Gd156 and p-p38-Pt198, but both conjugates were similarly capable to detect the induction p38 phosphorylation after PMA/ionomycin stimulation in various PBMC subsets. Histogram overlays of p-p38 staining in CD14+ monocytes are shown for comparison. Numbers reflect geoMSI.
Figure 2:
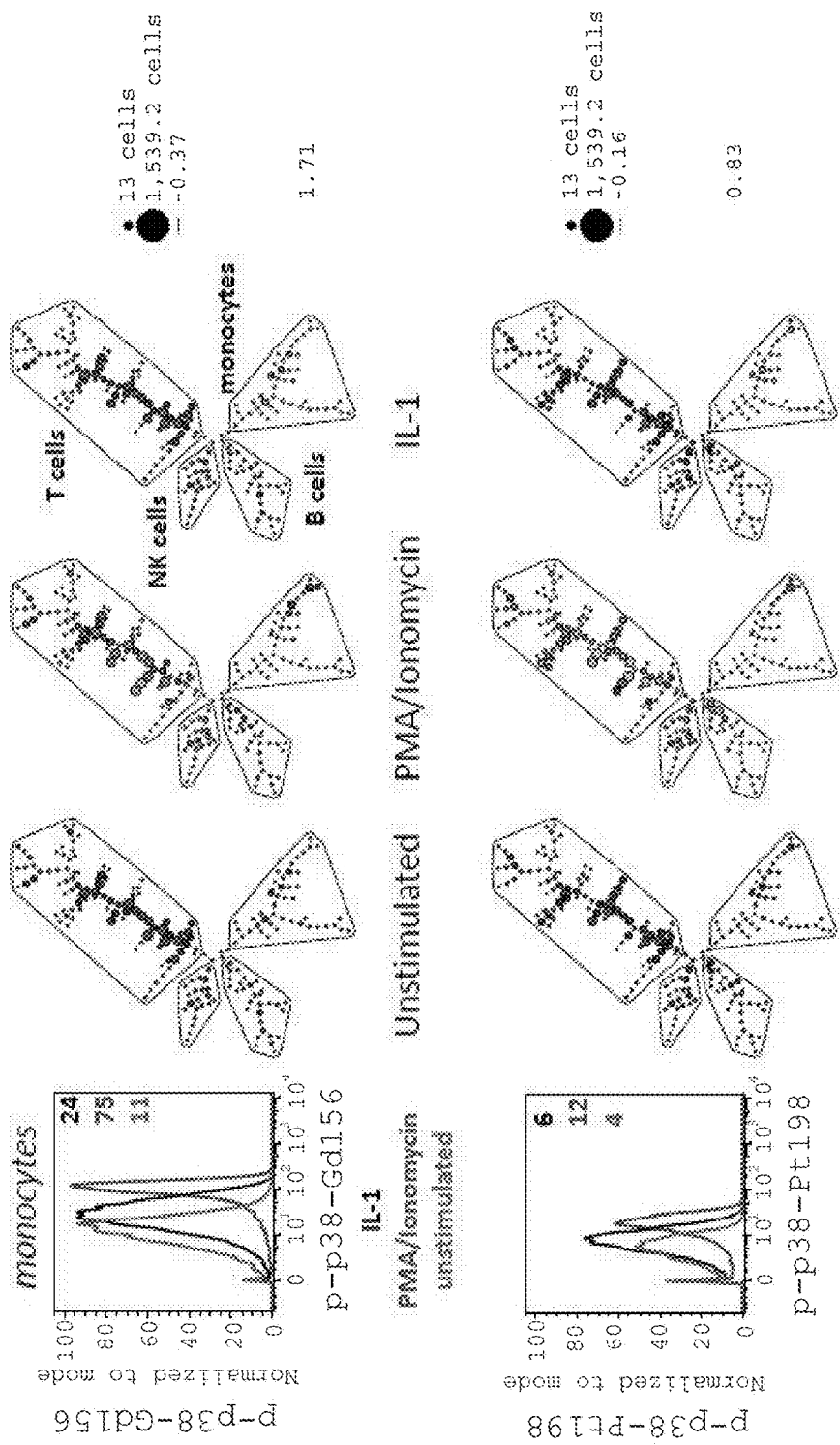

Application of Pt-labeled antibodies in surface, intracellular, and phosphoepitope-specific immunophenotyping After establishing the general utility of cisplatin-labeled Ab for mass cytometry, different Pt-conjugates were tested and comparisons were performed between data achieved with Pt-conjugates and lanthanide conjugates. FIG. 2A shows a CD4/CD8 staining of $CD3^+$ T cells using CD4-Pt194 and CD8-Pt198. As expected from previous analysis of T cells subsets using flow and mass cytometry, $CD4^+$ and $CD8^+$ T cells are both separated from background, and each other. Detection of CD4 and CD8 using the Pt conjugates was specific, as confirmed by blocking controls.

Spleen tyrosine kinase (Syk) was chosen as an example of an intracellular target analyte which shows gradually different expression levels on monocytes, B cells, NK cells and T cells (39). Whether lanthanide- and platinum-conjugated Ab would reproduce this pattern was investigated. Indeed, Syk-Nd150 and Syk-Pt198 showed the same staining pattern when analyzing Syk expression by subsets of PBMC (FIG. 2B), while geoMSI of Syk-Pt198 were about half of that of stainings with Syk-Nd150.

Next, a phosphoepitope-specific Pt198 conjugate was tested, detecting p38 phosphorylated at T180/Y182. It was compared to its commercially available counterpart conjugated to Gd156 in a PBMC stimulation experiment. Conventional analysis of monocytes in histograms confirmed that signal intensity of the Pt198 conjugate was lower than that of the lanthanide conjugate, but both gave essentially comparable results when comparing stimulation with PMA/ionomycin and IL-1 with unstimulated cells. A SPADE analysis of the same data confirmed that the same trends are picked up by an algorithmic data analysis tool, using the different conjugates (FIG. 2C). While PMA/ionomycin stimulation induced p38 phosphorylation across all major PBMC subsets, effects of IL-1 stimulation were confined to monocyte clusters using either the Pt198 or the Gd156 conjugate.

For Syk and p-p38 Abs, lanthanide conjugates provided higher signal intensities compared to their Pt-labeled counterparts, while the overall staining patterns achieved with platinum-conjugated Ab recapitulated those of lanthanide conjugated Abs. This data confirms the applicability of cisplatin-labeled Abs for surface, intracellular, and phosphoepitope-specific immune phenotyping.

Figure 3:
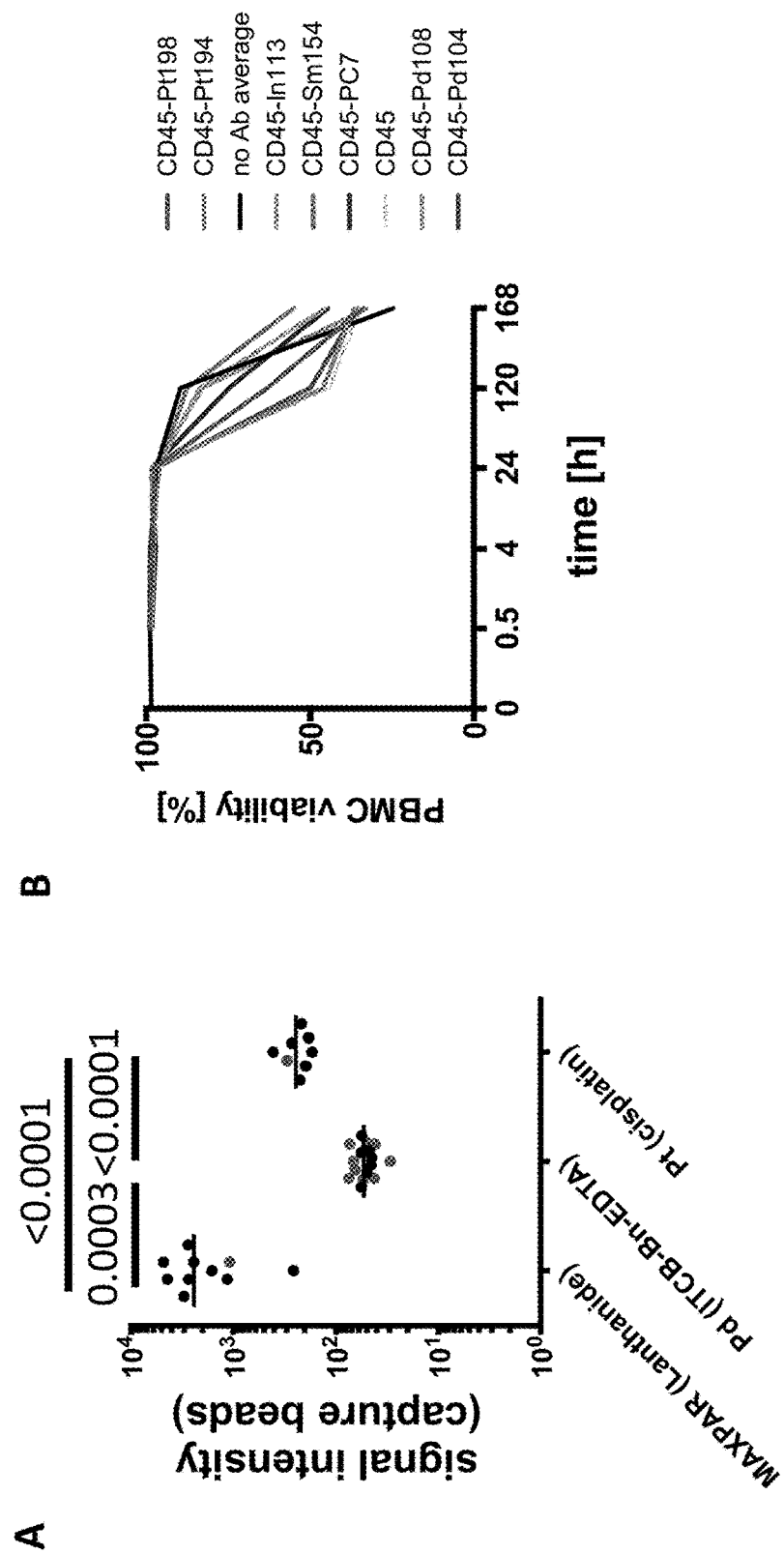
FIG. 3, Panels A-B. Properties of Pt-Ab-conjugates. (Panel A) Signals elicited by lanthanide-, platinum- and palladium-labeled Abs. Aliquots of Ab capture beads were single-stained with 1 µg/mL of eight Pt-Ab-conjugates, 16 Pd-Ab-conjugates and 10 lanthanide-Ab-conjugates. Signal intensities associated with the stained beads are shown. Horizontal bars indicate averages, that is 2428 for lanthanide conjugates, 245 for Pt conjugates, and 54 for Pd conjugates. Each dot represents one Ab conjugate. Red dots indicate conjugates of CD45 Ab (clone HI30). P values resulting from Wilcoxon testing (95% CI, two tailed) are indicated. (Panel B) Cytotoxicity analysis of Pt-labeled CD45 Ab. PBMC were cultured in the presence or absence of Pt-conjugated CD45 Ab or control CD45 Ab conjugates. PBMC viability was assessed at the indicated time points.

Signals elicited by platinum-vs. lanthanide-conjugated antibodies by using Ab capture beads stained were compared with a variety of lanthanide-, platinum-Ab-conjugates. Palladium-Ab-conjugates described before (13) were analyzed for comparison. At average, platinum conjugates showed ~10-fold lower signal intensity compared to lanthanide-conjugated Abs, and ~5-fold higher signal intensity compared to Pd-labeled Abs (FIG. 3A). This implicates that significantly less metal is associated to one Ab molecule when conjugated to Pt than when conjugated to a lanthanide using the MAXPAR® protocol. This notion was confirmed in an experiment aiming at determining metal loading per Ab. Ten Pt conjugates and twelve lanthanide conjugates made using the MAXPAR® kits (comprising purchased and in house made conjugates) were tested. At average, lanthanide conjugates carried 144 (SD, 42) metal ions per Ab molecule, while Pt conjugates carried 7 (SD, 2) ions per Ab.

Since the known cytotoxicity of cisplatin poses a potential concern to the use of cisplatin-conjugated Abs for labeling of live cells, the cytotoxicity of Pt-labeled CD45 Ab conjugates were analyzed in vitro. No evidence for increased PBMC death in the presence of Pt-labeled CD45 Ab for up to one day was found. For PBMC cultures lasting up to one week, the presence of Pt-labeled CD45 Ab was not associated with consistently different PBMC viability when compared to cultures without Ab or with differently labeled control CD45 Ab-conjugates (FIG. 3B). As a result, no evidence for cytotoxicity of Pt-Ab-conjugates was found.

Use of CD45-Pt Antibodies in Cell Surface Barcoding

Figure 4:
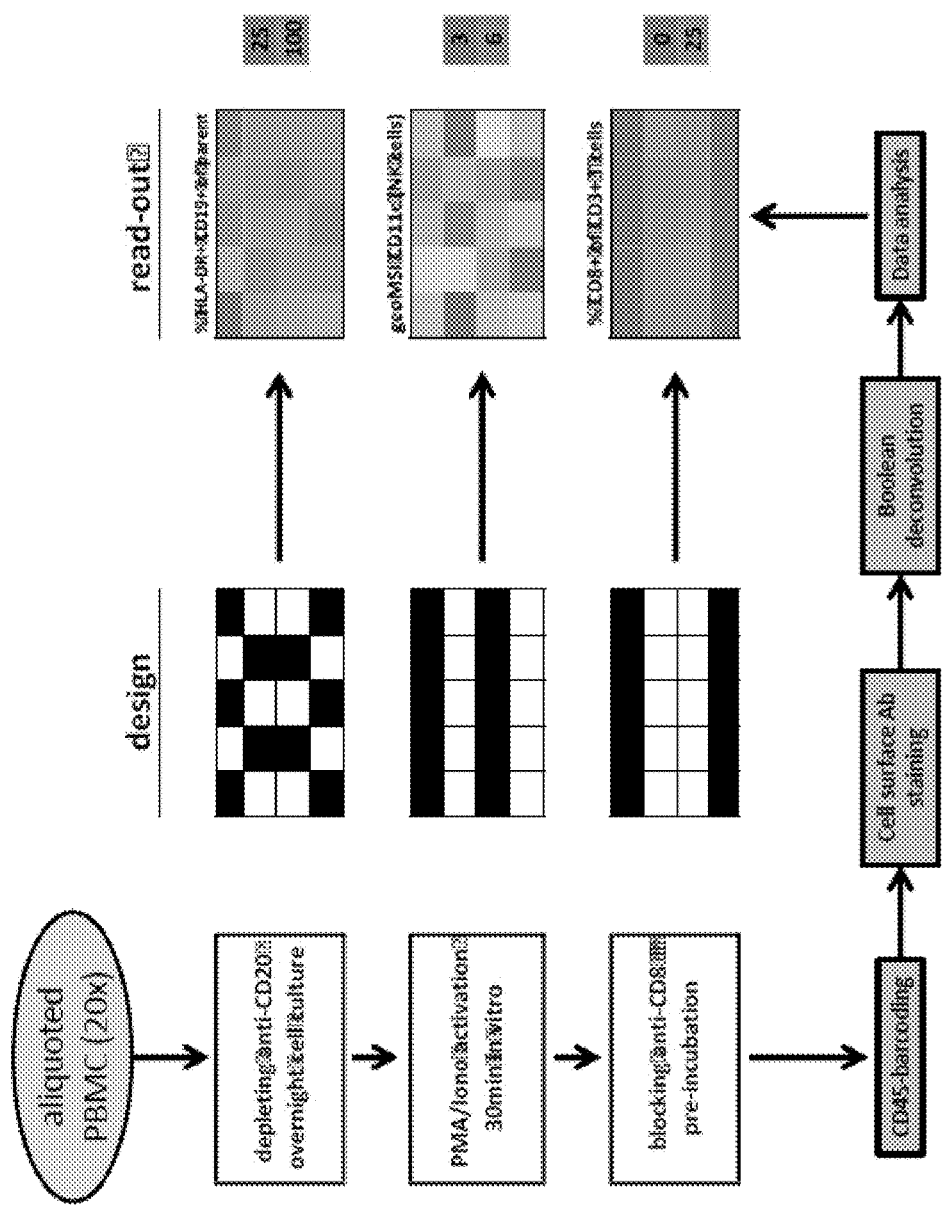
FIG. 4. Utility of CD45-Pt conjugates for CD45-barcoding. 20 aliquots of a single PBMC sample were treated in vitro with B cell depletion, PMA/ionomycin stimulation, and CD8 blockade, or combinations thereof, in the patterns specified in the black and white box schemes, in which each square represents one aliquot. After treatment, PBMC aliquots were CD45-barcoded, pooled, stained with a lineage marker Ab cocktail and acquired on a CyTOF version 2 mass cytometer. Data of individual aliquots were retrieved by Boolean deconvolution according to the gates shown for six different CD45 barcoding channels, including CD45-Pt194 and CD45-Pt198 (FIG. 5, Panel A). Data were analyzed for features revealing the effects of in vitro manipulations as detailed in FIG. 5, Panel B, and results were visualized as heatmaps organized like the black/white box schemes. Color legends are plotted next to the heatmaps.

Finally, CD45-Pt194 and CD45-Pt198 conjugates were used in a modified version of the previously described CD45-Ab-based cell surface barcoding strategy (13), together with CD45 Ab conjugated to Pd104, Pd106, Pd108, and Pd110. The success of barcoding was confirmed by the expected bimodal signal distribution in CD45 stainings of the pooled sample (FIG. 5A), and by successfully recovering differences in PBMC aliquots induced prior to barcoding, pooling and joint further processing (FIG. 4), a strategy that has been applied before to test barcoding methodologies (9,10).

Discussion

Ab can be conjugated to cisplatin, yielding platinum-labeled Ab that can be used for mass cytometry. Currently, two isotopically enriched cisplatins are available (at AM 194 and 198), which can be used to add two analyte-specific detection channels to existing panels. Assuming the future development of additional cisplatins carrying other isotopically enriched platinums, a total of six additional channels could be gained, at AM 190, 192, 194, 195, 196, and 198. Due to their very low natural abundance, Pt190 and Pt192 might be difficult to enrich to yield purities sufficient for application in mass cytometry. There is no overlap between these six and hitherto published reagents for mass cytometry, except for the application of cisplatin as a dead cell stain (7). The use of cisplatin-conjugated Ab and cisplatin as a dead cell staining is only compatible when different Pt isotopes are used in the reagents.

Spillovers from other reagents can occur: AM190 and AM192 signals can be caused by oxides of Yb 174 and Yb176, respectively, and right-leg spillover of the ion peak for the Iridium-191 and -193, frequently used in a DNA intercalating agent, can affect background signals at AM192 and AM194, respectively. However, in the experiment shown in FIG. 2A, CD20+ B cells showed negligible background in at AM194 (geoMSI, 0.45), in the presence of routine DNA staining (geoMSI at Ir193, 103) and in the presence of CD4-Pt194 and CD8-Pt198. Isotopic impurities of isotopically enriched platinum used for cisplatin production also need to be considered when using several cisplatin conjugates at the same time. Generally, the use of cisplatin-Ab conjugates is not recommended when analyzing samples from patients treated with cisplatin as a drug.

Ab conjugates made with isotopically enriched Pt/cisplatin have the advantage that all platinum contained each of in the reagents is collected in the respective single AM channel (as opposed to 6 channels for Pt*), thereby in theory increasing signal intensity. However, unlike in a MAXPAR® conjugation utilizing polymers to amplify the number of lanthanide ions bound to an antibody, in theory, a maximum of one Pt ion is attached per conjugation site on the Ab, resulting in overall lower signal intensities elicited by Pt-labeled Abs compared to MAXPAR®/lanthanide-labeled Abs. Therefore cisplatin-conjugates appear to be ideal for Abs detecting abundantly and stably expressed analytes.

The 20 nmol amount of cisplatin routinely used for Ab conjugation delivered robust results. As shown by the titration experiment, the procedure for Ab labeling also provides functional conjugates when using 5-fold higher or 5-fold lower amounts of cisplatin in the reaction, so that a certain tolerance can be concluded for the amount of cisplatin to use as well as for the availability of cisplatin binding sites which may differ between Abs.

Under safety aspects, amounts of cisplatin used for Ab labeling are small compared to a single therapeutic dose. 20 nmol per reaction compare to roughly 500 µmol in a therapeutic dose of 100 mg/m$^2$ (19). In addition, unbound cisplatin is separated from the conjugate after Ab labeling, so that toxicity for the lab personnel does not appear to be an important concern. The inability of the conjugate to stain dead cells, the typical purpose for cisplatin in mass cytometry (7), confirms the absence of reactive cisplatin in the final Ab preparation. It was also shown that Pt-labeled Abs are not cytotoxic per se, suggesting that they can be used to stain live cells without concerns regarding cytotoxicity.

To date, 23 platinum conjugations in a total of 7 labeling experiments have been performed, with 15 different Ab clones, 14 of which were successfully validated on PBMC (data not shown).

Based on that, routine use of cisplatin conjugates could be promising, while broader experience will show how versatile cisplatin conjugation is under different conditions, with different Ab clones, etc. Pt labeling with commercial cisplatin is very simple. It is quicker and less laborious compared to Pd labeling of Ab (13), and different from conjugation with lanthanides, it does not require loading of metal ions onto a chelator-decorated polymer. The procedure can be done in a few hours, using a protocol overlapping with that of MAXPAR® conjugations.

The availability of Ab-Pt conjugates expands the number of channels available for specific probes in mass cytometry experiments, and therefore contributes to efforts to fully exploit the CyTOF platform for systems immunology and biomarker discovery projects.

REFERENCES

1. Bendall S C, Simonds E F, Qiu P, Amir el A D, Krutzik P O, Finck R, Bruggner R V, Melamed R, Trejo A, Ornatsky O I and others. Single-cell mass cytometry of differential immune and drug responses across a human hematopoietic continuum. Science 2011; 332:687-96.

2. Tanner SD, Bandura DR, Ornatsky O, Baranov VI, Nitz M, Winnik MA. Flow cytometer with mass spectrometer detection for massively multiplexed single-cell biomarker assay. Pure and Applied Chemistry 2008; 80:2627-2641.

3. Ornatsky O, Bandura D, Baranov V, Nitz M, Winnik M A, Tanner S. Highly multiparametric analysis by mass cytometry. Journal of Immunological Methods 2010; 361: 1-20.

4. Behbehani G K, Bendall S C, Clutter M R, Fantl W J, Nolan G P. Single-cell mass cytometry adapted to measurements of the cell cycle. Cytometry A 2012; 81:552-66.

5. Edgar L J, Vellanki R N, Halupa A, Hedley D, Wouters B G, Nitz M. Identification of hypoxic cells using an organotellurium tag compatible with mass cytometry. Angew Chem Int Ed Engl 2014; 53:11473-7.

6. Newell E W, Sigal N, Bendall S C, Nolan G P, Davis M M. Cytometry by time-of-flight shows combinatorial cytokine expression and virus-specific cell niches within a continuum of CD8+ T cell phenotypes. Immunity 2012; 36:142-52.

7. Fienberg H G, Simonds E F, Fantl W J, Nolan G P, Bodenmiller B. A platinum-based covalent viability reagent for single-cell mass cytometry. Cytometry A 2012; 81:467-75.

8. Behbehani G K, Thom C, Zunder E R, Finck R, Gaudilliere B, Fragiadakis G K, Fantl W J, Nolan G P. Transient partial permeabilization with saponin enables cellular barcoding prior to surface marker staining. Cytometry A 2014.

9. Zunder E R, Finck R, Behbehani G K, Amir el A D, Krishnaswamy S, Gonzalez V D, Lorang C G, Bjornson Z, Spitzer M H, Bodenmiller B and others. Palladium-based mass tag cell barcoding with a doublet-filtering scheme and single-cell deconvolution algorithm. Nat Protoc 2015; 10:316-33.

10. Bodenmiller B, Zunder E R, Finck R, Chen T J, Savig E S, Bruggner R V, Simonds E F, Bendall S C, Sachs K, Krutzik P O and others. Multiplexed mass cytometry profiling of cellular states perturbed by small-molecule regulators. Nat Biotechnol 2012; 30:858-67.

11. Becher B, Schlitzer A, Chen J, Mair F, Sumatoh H R, Teng K W, Low D, Ruedl C, Riccardi-Castagnoli P, Poidinger M and others. High-dimensional analysis of the murine myeloid cell system. Nat Immunol 2014; 15:1181-9.

12. Leipold M D, Herrera I, Ornatsky O, Baranov V, Nitz M. ICP-MS-based multiplex profiling of glycoproteins using lectins conjugated to lanthanide-chelating polymers. J Proteome Res 2009; 8:443-9.

13. Mei H E, Leipold M D, Schulz A R, Chester C, Maecker H T. Barcoding of live human peripheral blood mononuclear cells for multiplexed mass cytometry. J Immunol 2015; 194:2022-31.

14. Horowitz A, Strauss-Albee D M, Leipold M, Kubo J, Nemat-Gorgani N, Dogan O C, Dekker C L, Mackey S, Maecker H, Swan G E and others. Genetic and environmental determinants of human NK cell diversity revealed by mass cytometry. Sci Transl Med 2013; 5:208ra145.

15. Strauss-Albee D M, Horowitz A, Parham P, Blish C A. Coordinated regulation of NK receptor expression in the maturing human immune system. J Immunol 2014; 193: 4871-9.

16. Majonis D, Ornatsky O, Kinach R, Winnik M A. Curious results with palladium- and platinum-carrying polymers in mass cytometry bioassays and an unexpected application as a dead cell stain. Biomacromolecules 2011; 12:3997-4010.

17. Rosenberg B, VanCamp L, Trosko J E, Mansour V H. Platinum compounds: a new class of potent antitumour agents. Nature 1969; 222:385-6.

18. Kelland L. The resurgence of platinum-based cancer chemotherapy. Nat Rev Cancer 2007; 7:573-84.

19. http://www.drugs.com/monograph/cisplatin.html.

20. Jordan P, Carmo-Fonseca M. Molecular mechanisms involved in cisplatin cytotoxicity. Cell Mol Life Sci 2000; 57:1229-35.

21. Cohen M S, Cai S, Xie Y, Forrest M L. A novel intralymphatic nanocarrier delivery system for cisplatin therapy in breast cancer with improved tumor efficacy and lower systemic toxicity in vivo. Am J Surg 2009; 198:781-6.

22. Boal A K, Rosenzweig A C. Crystal structures of cisplatin bound to a human copper chaperone. J Am Chem Soc 2009; 131:14196-7.

23. Ivanov A I, Christodoulou J, Parkinson J A, Barnham K J, Tucker A, Woodrow J, Sadler P J. Cisplatin binding sites on human albumin. J Biol Chem 1998; 273:14721-30.

24. Aull J L, Allen R L, Bapat A R, Daron H H, Friedman M E, Wilson J F. The effects of platinum complexes on seven enzymes. Biochim Biophys Acta 1979; 571:352-8.

25. Banci L, Bertini I, Blazevits O, Calderone V, Cantini F, Mao J, Trapananti A, Vieru M, Amori I, Cozzolino M and others. Interaction of cisplatin with human superoxide dismutase. J Am Chem Soc 2012; 134:7009-14.

26. Pizzo S V, Swaim M W, Roche P A, Gonias S L. Selectivity and stereospecificity of the reactions of dichlorodiammineplatinum(II) with three purified plasma proteins. J Inorg Biochem 1988; 33:67-76.

27. DeConti R C, Toftness B R, Lange R C, Creasey W A. Clinical and pharmacological studies with cis-diamminedichloroplatinum (II). Cancer Res 1973; 33:1310-5.

28. Schechter B, Pauzner R, Arnon R, Haimovich J, Wilchek M. Selective cytotoxicity against tumor cells by cisplatin complexed to antitumor antibodies via carboxymethyl dextran. Cancer Immunol Immunother 1987; 25:225-30.

29. Hata Y, Takada N, Sasaki F, Abe T, Hamada H, Takahashi H, Uchino J, Tsukada Y. Immunotargeting chemotherapy for AFP-producing pediatric liver cancer using the conjugates of anti-AFP antibody and anti-tumor agents. J Pediatr Surg 1992; 27:724-7.

30. McIntosh D P, Cooke R J, McLachlan A J, Daley-Yates P T, Rowland M. Pharmacokinetics and tissue distribution of cisplatin and conjugates of cisplatin with carboxymethyldextran and A5B7 monoclonal antibody in CD1 mice. J Pharm Sci 1997; 86:1478-83.

31. Schechter B, Arnon R, Wilchek M, Schlessinger J, Hurwitz E, Aboud-Pirak E, Sela M. Indirect immunotargeting of cis-Pt to human epidermoid carcinoma KB using the avidin-biotin system. Int J Cancer 1991; 48:167-72.

32. Falvo E, Tremante E, Fraioli R, Leonetti C, Zamparelli C, Boffi A, Morea V, Ceci P, Giacomini P. Antibody-drug conjugates: targeting melanoma with cisplatin encapsulated in protein-cage nanoparticles based on human ferritin. Nanoscale 2013; 5:12278-85.

33. Peng X H, Wang Y, Huang D, Wang Y, Shin H J, Chen Z, Spewak M B, Mao H, Wang X, Wang Y and others. Targeted delivery of cisplatin to lung cancer using ScFvEGFR-heparin-cisplatin nanoparticles. ACS Nano 2011; 5:9480-93.

34. Wang Y, Zhou J, Qiu L, Wang X, Chen L, Liu T, Di W. Cisplatin-alginate conjugate liposomes for targeted delivery to EGFR-positive ovarian cancer cells. Biomaterials 2014; 35:4297-309.

35. Werfel T, Witter W, Gotze O. CD11b and CD11c antigens are rapidly increased on human natural killer cells upon activation. J Immunol 1991; 147:2423-7.

36. Leipold M D, Maecker H T. Mass cytometry: protocol for daily tuning and running cell samples on a CyTOF mass cytometer. J Vis Exp 2012:e4398.

37. Chen T J, Kotecha N. Cytobank: providing an analytics platform for community cytometry data analysis and collaboration. Curr Top Microbiol Immunol 2014; 377:127-57.

38. Qiu P, Simonds E F, Bendall S C, Gibbs K D, Jr., Bruggner R V, Linderman M D, Sachs K, Nolan G P, Plevritis S K. Extracting a cellular hierarchy from high-dimensional cytometry data with SPADE. Nat Biotechnol 2011; 29:886-91.

39. Ishmael S S, MacGlashan D W, Jr. Syk expression in peripheral blood leukocytes, CD34+ progenitors, and CD34- derived basophils. J Leukoc Biol 2010; 87:291-300.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

What is claimed is:

1. A method of detecting whether an analyte is present on a particle, the method comprising:
    contacting the particle with an analyte-specific binding reagent conjugated to a platinum-containing moiety under conditions sufficient for analyte-specific binding of the analyte-specific binding reagent to the analyte present on the particle, wherein the platinum-containing moiety, when conjugated to the analyte-specific binding reagent, does not have covalent binding activity; and
    determining if the analyte-specific binding reagent conjugated with the platinum containing moiety is associated with the particle by detecting the platinum of the associated analyte-specific binding reagent by elemental mass spectrometry-based detection to detect whether the analyte is present on the particle;
    wherein the platinum-containing moiety is selected from the group consisting of cisplatin, carboplatin, oxaliplatin, nedaplatin, lobaplatin, heptaplatin, satraplatin, picoplatin, prolindac, lipoplatin, dichloridobis(isopropylamine)platinum(II) (JM-11), dichloridobis(cyclopentylamine)platinum(II) (NSC 170898), ormaplatin, sebriplatin, enloplatin, zeniplatin, spiroplatin, cycloplatam, miboplatin, iproplatin, [3-Acetyl-5-methyl-2,4(3H,5H)-furandionato-O3,O4][1,2-cyclo-hexanediamine-N,N']platinum(II) (TRK-710), aroplatin, and [trans-Diamminechloridoplatinum(II)][(μ-trans-diamminedihexanediamine-N,N')platinum(II)] (BBR3464).

2. The method of claim 1, wherein the platinum-containing moiety is conjugated directly to the analyte-specific binding reagent.

3. The method of claim 1, wherein the analyte-specific binding reagent is an antibody.

4. The method of claim 3, wherein the antibody is a phospho-specific antibody.

5. The method of claim 1, wherein the analyte-specific binding reagent is a nucleic acid.

6. The method of claim 1, wherein the particle is a cell.

7. The method of claim 1, wherein the analyte is a protein.

8. The method of claim 7, wherein the analyte is a phospho-specific isoform of the protein.

9. The method of claim 1, wherein the analyte is a nucleic acid.

10. The method of claim 1, wherein the analyte is a soluble analyte.

11. The method of claim 1, wherein the particle is present in a heterogeneous population of particles.

12. The method of claim 1, wherein the platinum in the platinum-containing moiety is a mixture of isotopes.

13. The method of claim 1, wherein the platinum in the platinum-containing moiety is synthetically enriched for a specific isotope.

14. The method of claim 1, wherein the platinum-containing moiety is cisplatin.

15. The method of claim 1, wherein multiple analyte-specific binding reagents are contacted with the particle, wherein each analyte-specific binding reagent is distinguishably labeled.

16. The method of claim 15, wherein each analyte-specific binding reagent is distinguishably labeled with platinum containing moiety having a different platinum isotope.

* * * * *